(12) United States Patent
Sinkus et al.

(10) Patent No.: US 11,921,183 B2
(45) Date of Patent: Mar. 5, 2024

(54) VIBRATION INDUCING APPARATUS FOR MAGNETIC RESONANCE ELASTOGRAPHY

(71) Applicant: King's College London, London (GB)

(72) Inventors: Ralph Sinkus, London (GB); Ondrej Holub, London (GB); Simon Lambert, London (GB); Rachel Clough, London (GB)

(73) Assignee: King's College London, London (GB)

( * ) Notice: Subject to any disclaimer, the term of this patent is extended or adjusted under 35 U.S.C. 154(b) by 645 days.

(21) Appl. No.: 15/553,933

(22) PCT Filed: Feb. 25, 2016

(86) PCT No.: PCT/GB2016/050490
§ 371 (c)(1),
(2) Date: Aug. 25, 2017

(87) PCT Pub. No.: WO2016/135493
PCT Pub. Date: Sep. 1, 2016

(65) Prior Publication Data
US 2018/0172789 A1 Jun. 21, 2018

(30) Foreign Application Priority Data
Feb. 25, 2015 (GB) ...................................... 1503177

(51) Int. Cl.
*G01R 33/563* (2006.01)
*A61B 5/00* (2006.01)
(Continued)

(52) U.S. Cl.
CPC ...... *G01R 33/56358* (2013.01); *A61B 5/0051* (2013.01); *A61B 5/055* (2013.01); *G01R 33/28* (2013.01); *G01R 33/56308* (2013.01)

(58) Field of Classification Search
CPC ... A61B 5/0051; A61B 5/0048; A61B 5/0057; A61B 5/055; B06B 1/10; B06B 1/12;
(Continued)

(56) References Cited

U.S. PATENT DOCUMENTS 3,735,757 A * 5/1973 MacFarland ....... A61H 23/0263
601/72
4,098,266 A 7/1978 Muchisky et al.
(Continued)

FOREIGN PATENT DOCUMENTS

CN 1777817 A 5/2006
CN 101406395 A 4/2009
(Continued)

OTHER PUBLICATIONS

Plewes et al. "Visualization and quantification of breast cancer biomechanical properties with magnetic resonance elastography" Phys. Med. Biol. 45 (2000) 1591-1610 (Year: 2000).*
(Continued)

*Primary Examiner* — Boniface Ngathi
*Assistant Examiner* — Milton Truong
(74) *Attorney, Agent, or Firm* — SHOOK, HARDY & BACON L.L.P.

(57) ABSTRACT

A magnetic resonance (MR) compatible transducer for magnetic resonance elastography applications has a cantilevered drive element a free end of which is arranged in use to move reciprocally, and a flexible non-conductive connection rod slidably disposed within a flexible non-conductive sleeve. The connection rod is affixed at a proximal end to the cantilevered drive element via a proximal flexible connection piece that in use accommodates the slight rotational movement of the cantilevered drive element as it reciprocates about its secured end, whilst translating the rotational reciprocation of the cantilevered drive element into a pure
(Continued)

translational reciprocation of the connection rod within the sleeve. The distal end of the connection rod is affixed against a protrusion connected to another cantilevered driven element, upon which is mounted a piston element that in use contacts the subject. The distal end of the connection rod is provided with a distal flexible connection piece that forms the connection between the end of the connection rod and the cantilevered driven element, again to account for the pure translational movement of the rod being converted to rotational movement of the cantilevered driven element about its cantilever pivot point.

20 Claims, 25 Drawing Sheets

(51) Int. Cl.
  *A61B 5/055* (2006.01)
  *G01R 33/28* (2006.01)

(58) Field of Classification Search
  CPC .... B06B 1/16; G01R 33/28; G01R 33/56308; G01R 33/56358; G01R 33/56375; A61H 23/0263
  See application file for complete search history.

(56) References Cited

U.S. PATENT DOCUMENTS

| | | | |
|---|---|---|---|
| 5,388,469 A * | 2/1995 | Woltering | F03G 3/00 74/61 |
| 5,427,107 A | 6/1995 | Milo et al. | |
| 5,952,828 A | 9/1999 | Rossman et al. | |
| 8,981,682 B2 | 3/2015 | Delson et al. | |
| 9,482,733 B2 | 11/2016 | Fuderer | |
| 2003/0220556 A1 | 11/2003 | Porat et al. | |
| 2006/0258934 A1 | 11/2006 | Zenge et al. | |
| 2007/0236213 A1 | 10/2007 | Paden et al. | |
| 2009/0200880 A1 | 8/2009 | Mortimer et al. | |
| 2010/0049029 A1 * | 2/2010 | Li | A61B 5/055 600/410 |
| 2010/0130856 A1 | 5/2010 | Sack et al. | |
| 2010/0249511 A1 * | 9/2010 | Miyagi | A61B 1/0011 600/139 |
| 2011/0245658 A1 * | 10/2011 | Numano | G01R 33/56358 600/421 |
| 2012/0229400 A1 | 9/2012 | Birnbaum et al. | |
| 2012/0232780 A1 * | 9/2012 | Delson | A63F 13/803 701/400 |
| 2013/0237807 A1 | 9/2013 | Maitre et al. | |
| 2013/0239690 A1 * | 9/2013 | Tadano | G01R 33/56358 73/644 |
| 2015/0080773 A1 * | 3/2015 | Godfrey | A61H 1/00 601/70 |
| 2015/0148663 A1 * | 5/2015 | Vernickel | G01R 33/3415 600/422 |
| 2016/0038030 A1 * | 2/2016 | Smith | G01B 9/02025 600/427 |
| 2016/0213350 A1 * | 7/2016 | Lee | A61B 8/4483 |
| 2016/0258758 A1 * | 9/2016 | Houston | G01C 21/20 |

FOREIGN PATENT DOCUMENTS

| | | |
|---|---|---|
| CN | 101675356 A | 3/2010 |
| CN | 202198595 U | 4/2012 |
| CN | 202386685 U | 8/2012 |
| CN | 102782518 A | 11/2012 |
| CN | 103620928 A | 3/2014 |
| CN | 104006899 A | 8/2014 |
| DE | 1928876 B1 | 1/1971 |
| JP | S56137074 U | 10/1981 |
| JP | S62-105012 A | 5/1987 |
| JP | H02-131494 U | 11/1990 |
| JP | 2002010991 A | 1/2002 |
| JP | 2002-136758 A | 5/2002 |
| JP | 2006-218069 A | 8/2006 |
| JP | 2007-519099 A | 7/2007 |
| JP | 2008-003897 A | 1/2008 |
| JP | 2011-098158 A | 5/2011 |
| JP | 2011-522598 A | 8/2011 |
| JP | 2013-239194 A | 11/2013 |
| JP | 2015-519168 A | 7/2015 |
| WO | 2011/055469 A1 | 5/2011 |
| WO | 2012/026543 A1 | 3/2012 |
| WO | 2013186658 A2 | 12/2013 |
| WO | 2014128593 A1 | 8/2014 |
| WO | 2014/188368 A1 | 11/2014 |
| WO | 2016135493 A2 | 9/2016 |

OTHER PUBLICATIONS

Cutfield et al. "Visual and proprioceptive interaction in patients with bilateral vestibular loss". NeuroImage: Clinical 4 (2014) 274-282 (Year: 2014).*

Guo J. et al.: "3D multifrequency abdominal MR elastography using a piezoelectric driver. single-shot wave-field acquisition. and multifrequency dual parameter inversion", Proceedings of the International Society for Magnetic Resonance in Medicine. 21st Annual Meeting, Apr. 7, 2013 (Apr. 7, 2013), p. 2430, XP040630026, Utah, USA.

Sack I et al: "Magnetic resonance elastography of the liver; Magnetresonanzelastographie der Leber", Der Radiologe; Zeitschrift Fur Diagnostische Und Interventionelle Radiologie. Radioonkologie, Nuklearmedizin, Springer, Berlin, DE, vol., No. 8, Jul. 11, 2012 (Jul. 11, 2012). pp. 738-744. XP035100673.

Oida T et al: "Magnetic resonance elastography : in vivo measurements of elasticity for human tissue", Informatics Research for Development of Knowledge Society Infrastructure.,2004, ICKS 2004. International Conference on Kyoto, Japan Mar. 1-2, 2004. Piscataway, NJ, USA, IEEE, Mar. 1, 2004 (Mar. 1, 2004), pp. 57-64, XP010709590.

Tse Z T H et al: "Magnetic resonance elastography hardware design: a survey", Proceedings of the Institution of Mechanical Engineers, Journal of Engineering in Medicine, Part H, Mechanical Engineering Publications Ltd, London, GB, vol. 223, No. 4, May 1, 2009 (May 1, 2009), pp. 497-514, XP009163292.

Nicholas J. Cutfield et al: "Visual and proprioceptive interaction in patients with bilateral vestibular loss", Neuroimage: Clinical. vol. 4. Jan. 1, 2014 (Jan. 1, 2014). pp. 274-282, XP055295660.

IPO Search Report under Section 17 dated Jul. 15, 2015 in UK Patent Application No. GB1503177.6, 1 page.

International Search Report and Written Opinion dated Aug. 25, 2016 in International Patent Application No. PCT/GB2016/050490, 22 pages.

International Preliminary Report on Patentability dated Aug. 29, 2017 in International Patent Application No. PCT/GB2016/050490, 15 pages.

Cutfield, Nicholas J., Gregory Scott, Adam D. Waldman, David J. Sharp, and Adolfo M. Bronstein. "Visual and proprioceptive interaction in patients with bilateral vestibular loss." NeuroImage: Clinical 4 (2014): 274-282.

Notice of Reasons for Refusal dated Oct. 21, 2019 in Japanese Patent Application No. 2017-545571, 9 pages.

Notification of Reasons for Refusal received for Japanese Patent Application No. 2017-545571, dated Jun. 9, 2020, 8 pages.

First Office Action and Search received for Chinese Patent Application No. 201680012277.3, dated Feb. 24, 2021, 19 pages. (English Translation Submitted).

Notice of Reasons for Refusal received for Japanese Patent Application No. 2017-545571, dated Aug. 3, 2021, 5 pages. (English Translation Submitted).

Rodriguez, Y., et al., "Vibration Detection Using Optical Fiber Sensors", Journal of Sensors, vol. 2010, Article ID 936487, pp. 1-13 (2010).

(56) References Cited

OTHER PUBLICATIONS

Office Action received for European Patent Application No. 16707536.5, dated Nov. 3, 2020, 5 pages.
Notice of Reasons for Refusal received for Japan Patent Application No. 2017-545571, dated Jan. 19, 2021, 7 pages.
"Variable speed wind turbine", Wikipedia, Retrived from Internet URL : https://en.wikipedia.org/wiki/Variable_speed_wind_turbine#Stall_regulated, accessed on Dec. 30, 2021, pp. 9.
Gizewski, E. R., et al., "Cerebral activation using a MR-compatible piezoelectric actuator with adjustable vibration frequencies and in vivo wave propagation control", NeuroImage, vol. 24, pp. 723-730 (2005).
Jauch, C., "Stability and Control of Wind Farms in Power Systems", Riso National Laboratory, Retrived from Internet URL : https://www.osti.gov/etdeweb/servlets/purl/20811926, pp. 202 (Oct. 2006).
Koerner, H., et al., "Photogenerating work from polymers", Materials Today, vol. 11, No. 7-8, pp. 34-42 (2008).
Mariappan, Y. K., et al., "Magnetic Resonance Elastography: A Review", Clinical Anatomy vol. 23. No. 5, pp. 497-511 (2010).
Ohm, C., et al., "Applications of Liquid Crystalling Elastomers", Adv Polym Sci, vol. 250, pp. 49-94 (2012).
White, T. J., et al., "A high frequency photodriven polymer oscillator", Soft Matter, vol. 4, pp. 1796-1798 (2008).
First Office Action and Search Report received for Chinese Patent Application No. 201680012277.3, dated Dec. 4, 2019, 18 pages. (English Translation Submitted).
Office Action received for European Patent Application No. 16707536.5, dated Mar. 13, 2020, 5 pages.
Second Office Action received for Chinese Patent Application No. 201680012277.3, dated Aug. 17, 2020, 17 pages. (English Translation Submitted).
Notification to Grant and Search received for Chinese Patent Application No. 201680012277.3, dated Jun. 3, 2021, 5 pages. (English Translation Submitted).
Office Action received for European Patent Application No. 16707536.5, dated Sep. 20, 2021, 4 pages.
Decision to Grant received for Japanese Patent Application No. 2017-545571, dated Oct. 26, 2021, 6 pages. (English Translation Submitted).
Carl von Ossietzky, "Forced Mechanical Oscillations", University Oldenburg, Institute of Physics Module Introductory Course Physics (12 pages).
Wikipedia contributors, "Resonance," Wikipedia, The Free Encyclopedia, https://en.wikipedia.org/w/index.php?title=Resonance&oldid=1152617080 (accessed May 1, 2023).

* cited by examiner

[1] – MR bore ; [2] – MR table ; [3] – Patient ; [4] – MRE transducer front-end ; [5] – metal-free flexible rod; [6] – electromagnetic driver; [7] – RF filter; [8] - fMRI trigger (X1 or "trigger black box");

VIBRATION INDUCING APPARATUS FOR MAGNETIC RESONANCE ELASTOGRAPHY

TECHNICAL FIELD

Embodiments of the present invention relate to a vibration inducing apparatus for inducing vibrations in the anatomy of a subject during magnetic resonance (MR) based measurements.

BACKGROUND TO THE INVENTION AND PRIOR ART

The detection of pathological tissue alterations by manual palpation is a simple but essential diagnostic tool, which has been applied by physicians since the beginning of medicine. Recently, the virtual "palpation" of tissue has become feasible using a method called MR-elastography (MRE). With many pathologies such as cancer, cardiovascular diseases, and neuro-degenerative diseases impacting biomechanics, the potential of this method for early diagnosis, staging, and therapy follow up is enormous. Recent clinical and pre-clinical results in the domains of liver fibrosis and multiple sclerosis have demonstrated impressive initial results. MRE quantifies in-vivo biomechanical properties of tissue by analyzing the propagation of externally elicited shear waves. The general concept of this method requires three steps:
1. sending low-frequency mechanical waves into the body via an externally applied mechanical transducer,
2. imaging those waves via dedicated MR-motion sensitized sequences, and
3. generating from those data via an inversion process images of the biomechanical properties.

Various mechanisms have been proposed in the prior art for the controllable generation of the mechanical waves, and for the designs of the required mechanical transducer. FIG. 1 illustrates one arrangement from U.S. Pat. No. 5,952,828, which discloses a transducer 10 suitable for applying an oscillatory stress externally to a patient. The transducer 10 includes a coil of wire 11 wound on a bobbin 12, with the coil axis 14 directed perpendicular to the polarizing magnetic field BO of the MR scanner. The coil 11 is 400 turns of 30 AWG copper wire, and its leads 16 are connected directly to an amplifier. Any coil which is wound until the impedance is 8 ohms could be employed. The bobbin 12 is mounted to a flexible arm 18 that is attached to, and cantilevered from a supporting block 20. When a current passes through the coil 11, the magnetic field which it produces interacts with the polarizing field BO of the MRI system. The bobbin 12 is thus twisted to bend the flexible arm 18 either upward or downward depending on the direction of current flow. By alternating the direction of current flow, the coil 11 twists back and forth to produce a corresponding alternating force which causes the flexible arm 18 to oscillate as indicated by the arrow 22. A strap 21 extends through an opening in the supporting block 20 and securely fastens it to the patient.

The oscillatory motion of the arm 18 is coupled to the subject 30 by an applicator 24. In its simplest form the applicator 24 is comprised of a tube 26 of the desired length which is secured at one of its ends to the arm 18. A pressure plate 28 is secured to the other end of the tube 26. The pressure plate 28 rests on the subject 30 to be imaged and its oscillatory movement produces a corresponding oscillatory compressive force that generates the desired synchronous motion.

U.S. Pat. No. 5,952,828 therefore describes using the magnetic field BO of the MRI scanner itself to drive the coil 12. However, this can introduce issues in that the coil 12, being conductive, can introduce artefacts in the images produced if the arrangement is placed too close to the subject being imaged. To get around this problem, pneumatic or acoustic driven arrangements have also been developed. FIG. 2 illustrates two such arrangements taken from Tse, Z. T. H. et al. *Magnetic resonance elastography hardware design: a survey* Proc IMechE Vol 223 Part H:J Engineering in Medicine, p. 497-514, 5 Jan. 2009. FIG. 2(*a*) shows a system for MRE examination of the liver which consists of a loudspeaker for vibration generation which is placed outside the scanner room to avoid any EM interference, and a passive driver placed on the patient body. Mechanical vibration by the speaker is transmitted to the end effector via a pneumatic tube allowing a separation of the magnetic components and electronics control system from the scanner room. However, phase lag in mechanical motion and difficulty in synchronization control are the intrinsic problems of a pneumatic system as air is an easily compressible medium for power transmission and therefore high bandwidth is difficult to achieve in the system. As synchronization of the mechanical excitation to the scan sequence is an important step in achieving stable MRE images and also determines the wavelength and hence the accuracy of the shear modulus estimation of the target area, it is always desirable to optimize the mechanical control. Because of the difficulty in synchronizing the vibration device to the image sequence, pneumatic actuators are only adapted for applications with low frequencies up to 100 Hz.

A design based on a loudspeaker with a long carbon fiber rod for transmission was demonstrated by Sack et al. *Non-invasive measurement of brain viscoelasticity using magnetic resonance elastography* NMR Biomedicine, Vol. 21 pp. 265-271, 2008. FIG. 2(*b*) and FIG. 4 illustrate this arrangement. Here, the mechanical vibration from a speaker is transmitted to a head rocker unit with a 2.8 m rigid carbon fiber rod which assists the synchronization issue. The head rocker is attached to the head skin to excite the brain tissue and is designed to be adaptable with a standard MRI head coil, as shown in FIG. 2(*b*) and FIG. 4. Using a carbon fiber rod for the actuation medium eliminates the inconsistent phase lag problem of the pneumatic system, but the head rocker is mounted stiffly on the fiber rod and thus sacrifices its flexibility for different orientations. The loudspeaker and the control electronics need to be placed in the scanner room (although far from the isocentre), leading to a certain amount of SNR degradation and potentially inducing an attractive force or torque and EM interference.

Mariappan et al in *Magnetic Resonance Elastography: A Review* Clinical Anatomy vol. 23: pp 497-511 (2010) also reviewed the mechanical actuator technology for MRE, and identified the most commonly used driving mechanisms, as shown in FIGS. 3(*b*) to (*d*). FIG. 3(*a*) shows the basic functional blocks of all MRE drivers known in the art, in that a function generator synchronized with the MR pulse sequence is typically used to control the mechanical driver, usually via some sort of amplifier. FIG. 3(*b*) shows an electromechanical driver that works via the Lorentz force and utilizes the magnetic field of the main MRI magnet—the same arrangement is also disclosed in U.S. Pat. No. 5,952, 828, discussed above. A piezo-electric stack driver system is shown in FIG. 3(*c*), where the motion created is based on the piezo-electric property of certain materials. Focused-ultra-sound-based (FUS-based) radiation force has also been investigated as a means to create mechanical motion for various elasticity imaging strategies including MRE, where shear waves are created directly within tissue with externally placed ultrasound transducers.

Further according to Mariappan, and reflecting the findings of Tse et al., ibid, another widely used method of creating the required vibrations for MRE utilizes the motion of the voice coils used in acoustic speaker systems. The required vibrations are again produced by the Lorentz force, but the static magnetic field is from a devoted permanent magnet present in the acoustic speaker. These speakers, with their own permanent magnets, have to be placed away from the main MR magnet, thus this system necessitates an additional component to couple the vibrations produced by the speakers to the tissue. One approach is to enclose the area around the speaker cone or its equivalent, to use a long connecting tube to pneumatically conduct the harmonic pressure variations of the air into the scanner and to terminate the tube in a passive drum-like driver kept in contact with the tissue (pressure-activated driver, shown schematically in FIG. 3(d)). This driver can be easily manipulated, and the portion of the driver system actually in the vicinity of the patient is made out of materials that do not produce MR image artifacts. As the actual vibrations are produced by an active component different from the passive component in contact with the tissue, the passive component can be adapted to suit any organ of interest, such as the breast or brain. The amplitude of the vibrations induced within the tissue is very low and is maintained within vibration safety limits.

Thus, as will be apparent from the above, the prior art arrangements typically fall into three main categories. There are the BO driven arrangements of U.S. Pat. No. 5,952,828, which provide for good mechanical connectivity and vibration reproducibility, but which typically require the drive coil to be too close to the MRI scanner, and hence introduce imaging artifacts. Then there are the pneumatically driven arrangements, typically using a speaker cone or the like as the vibration driver, which permit the driver to be located well away from the scanner, but depend on pneumatic conduction of the vibration. As mentioned, above, such arrangements suffer from the problem that the resolution and frequency of the vibration transmitted to the subject being imaged is low, due to the pneumatic vibration conduction.

The third category tries to get around both of these problems by using an acoustic driver (loudspeaker) located well away from the MRI scanner itself and hence improving MR compatibility, but with a rigid vibration transmission rod to transmit to vibrations to the patient, this overcoming the issues of the pneumatic systems. The Sacks et al. arrangement discussed above reflects this approach. However, as discussed above, and as appreciated by Tse et al., the drawback of this arrangement (shown in FIG. 4) is that it is inflexible and does not allow vibrations to be applied to any part of the body as may be desired. Instead, the arrangement is limited to the use of the head cradle, with the rigid rod running the length of the subject's body, as shown in FIG. 4. Many subjects will find such an arrangement intimidating.

SUMMARY OF THE INVENTION

Some embodiments of the invention provide a magnetic resonance compatible transducer for magnetic resonance elastography applications having a cantilevered drive element, a free end of which is arranged in use to move reciprocally, and a flexible non-conductive connection rod slidably disposed within a flexible non-conductive sleeve. The rod and the sleeve are of sufficient length (typically in excess of 0.50 m) such that the cantilevered drive element can remain outside of the bore of the MRI machine, whilst the rod within the sleeve extend thereinto. The connection rod is affixed at a proximal end to the cantilevered drive element via a proximal flexible connection piece that in use accommodates the slight rotational movement of the cantilevered drive element as it reciprocates about its secured end, whilst translating the rotational reciprocation of the cantilevered drive element into a pure translational reciprocation of the connection rod within the sleeve. The distal end of the connection rod is affixed against a protrusion connected to another cantilevered driven element, upon which is mounted a piston element that in use contacts the subject.

In some embodiments the piston element is arranged to extend substantially orthogonal to the plane of the cantilevered driven element, whereas in other embodiments the piston element may be arranged at different angles to the plane of the cantilevered driven element, for example at any acute angle thereto. The distal end of the connection rod is provided with a distal flexible connection piece that forms the connection between the end of the connection rod and the cantilevered driven element, again to account for the pure translational movement of the rod being converted to rotational movement of the cantilevered driven element about its cantilever pivot point.

In one embodiment the cantilevered drive element has a coil of wire affixed thereon, and through which in use an alternating current is fed. This current then interacts with the BO field of the MRI scanner to cause the coil to move, reciprocally back and forth, thus reciprocally moving the cantilevered drive element to which the coil is affixed. Using the BO field of the scanner to provide motive force for a mechanical actuator is known from U.S. Pat. No. 5,952,828, discussed above.

In other embodiments, instead of using a coil of wire and the BO field, other motive mechanisms may be used. For example, in one embodiment a clockwork mechanism that is arranged to rotate an off-center weight may be mounted on the end of the cantilevered drive element. Such a clockwork mechanism may be made completely from plastics material so as to be MRI compatible, thus allowing the whole transducer to be placed in the MRI bore if necessary, without causing image artifacts.

In another embodiment, the cantilevered drive element may instead be targeted by a high power laser that fires laser pulses at the free end of the drive element. The impact of the high energy photons on the cantilevered drive element (particularly if provided with a blackened target thereon) should be sufficient to cause sufficient movement of the cantilevered drive element to drive the transducer.

In further embodiments, the cantilevered driven element is used solely, driven directly by an electromagnetically activated crystal, such as a piezo-electric crystal, or a photo-mechanical crystal. Use of such drive crystals allows for MR safe arrangements to be provided that do not require the connection rod to a drive mechanism located outside of the MR bore, and hence more compact arrangements are obtained.

In view of the above, one embodiment provides a magnetic resonance (MR) compatible transducer for magnetic resonance elastography, comprising: a cantilevered drive element, a free end of which is arranged in use to move reciprocally under a motive force; a flexible non-conductive connection rod slidably disposed within a flexible non-conductive sleeve, the rod being affixed at a proximal end thereof to the cantilevered drive element; and a cantilevered driven element, upon which is mounted a piston element that in use contacts the subject, the driven element being affixed to a distal end of the connection rod; the arrangement being such that reciprocal motion of the cantilevered drive element under the motive force is transferred via the connection rod to the cantilevered driven element.

Another embodiment provides a magnetic resonance (MR) compatible transducer for magnetic resonance elastography, comprising: a cantilevered driven element, upon which is mounted a piston element that in use contacts a subject; and a crystal-based drive arrangement, having a drive crystal arranged in use to exert a motive force on the cantilevered driven element so as to cause, in use, oscillation thereof.

In this embodiment the crystal-based drive arrangement may comprise an opto-mechanical crystal, and means for illuminating the opto-mechanical crystal. Optionally the means for illuminating the opto-mechanical crystal comprise a light source, and a waveguide arranged to guide light from the light source so as to be incident on the opto-mechanical crystal. In one embodiment the means for illuminating are arranged in use to repeatedly illuminate the opto-mechanical crystal so as to cause oscillatory movement thereof. The light source should be able to produce light of different wavelengths, and the change in wavelength of the incident light causes the oscillatory movement of the crystal.

In another embodiment the crystal based drive arrangement comprises a piezo-electric crystal, and means for applying an electric field to the piezo-electric crystal. In this embodiment the means for applying an electric field to the piezo-electric crystal may comprise an electrical signal generator and an electrical conductor. Moreover, the electrical signal generator may be arranged to supply the piezo-electric crystal with a plurality of electrical pulses so as to cause oscillatory movement thereof.

In a further embodiment a different arrangement is used, which relies on rotation of an eccentric mass to generate the vibrations needed for MRE. The mass is driven by an MR compatible rotating drive shaft from a motor, for example a drive shaft made from phosphor bronze. The drive shaft is preferably flexible to allow ease of positioning of a vibrator box containing the eccentric mass against a subject to be imaged. In some embodiments multiple eccentric masses that are driven at different speeds, for example via an arrangement of gears from a single rotational drive input, can be provided to provide multiple vibration frequencies simultaneously. Moreover, in some embodiments, multiple vibrator boxes may be prepositioned on a substrate that is then placed against a subject to be imaged, in order to ensure accurate relative positioning of multiple vibrator boxes according to clinical imaging need.

In view of this further embodiment, one aspect of the invention further provides a magnetic resonance (MR) compatible transducer for magnetic resonance elastography, comprising: a rotationally mounted eccentric mass arranged to rotate within a container having at least one outer surface that in use transmits vibrations to contacting objects; a drive shaft, functionally connected to the rotationally mounted eccentric mass and arranged to impart rotational energy to the rotationally mounted eccentric mass; wherein the mass, container, and drive shaft are made from MR compatible material.

Further features and advantages will be apparent from the appended claims.

BRIEF DESCRIPTION OF THE DRAWINGS

Embodiments of the invention will now be described with reference to the accompanying drawings, wherein like reference numerals refer to like parts, and wherein.

OVERVIEW OF EMBODIMENTS

Embodiments of the present invention aim to provide controlled and non-distorted oscillating stress to a subject under MRE assessment. Some embodiments of the invention employ an electrically energized coil positioned remotely to the subject as a driver, while the mechanical waves generated by the driver are transmitted via a semi-flexible rod guided to a front-end transducer which is in direct contact with the subject.

Figure 6:
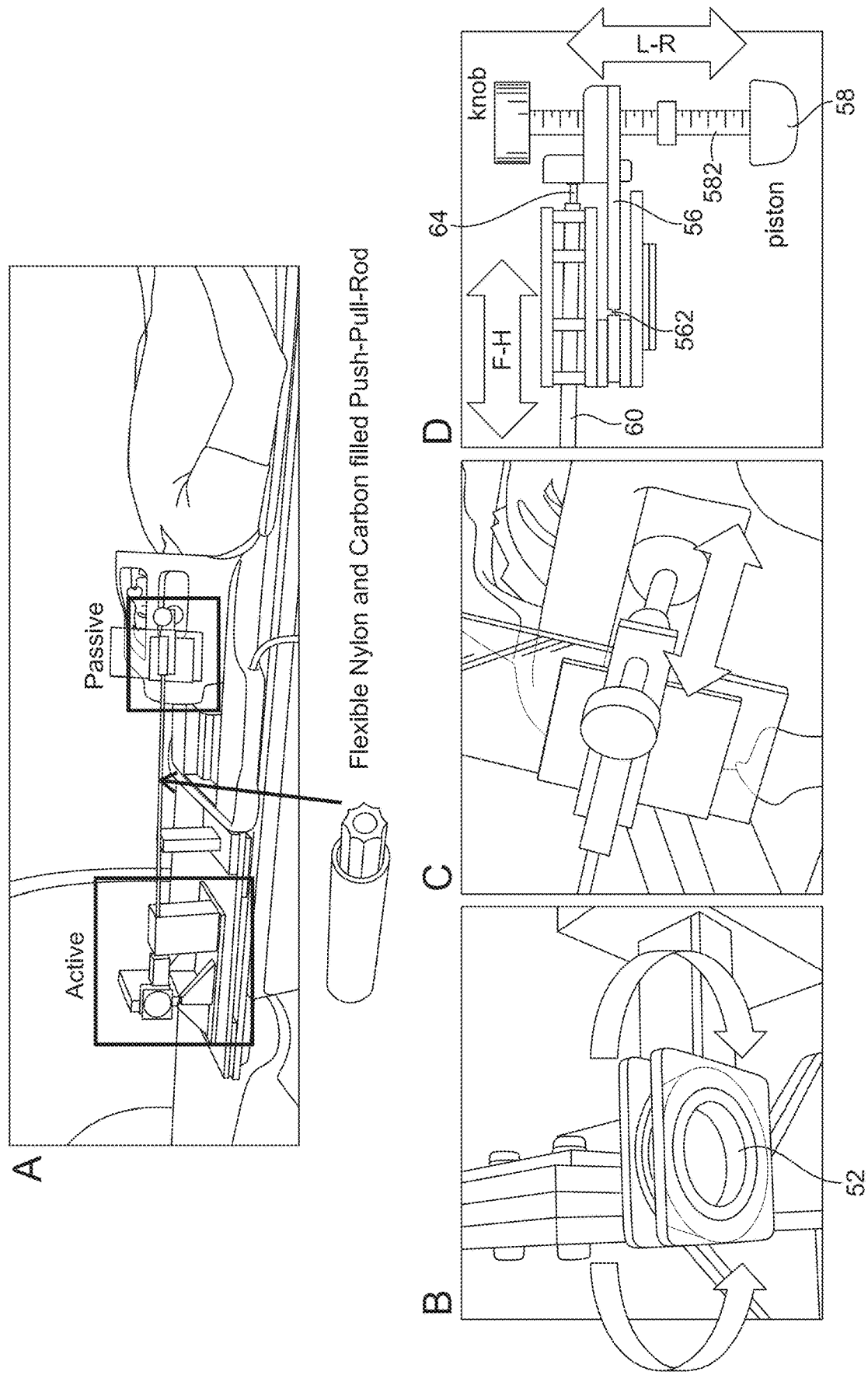
FIGS. 6(a) to (d) are photographs of various elements of the first embodiment of the invention.
Figure 7:
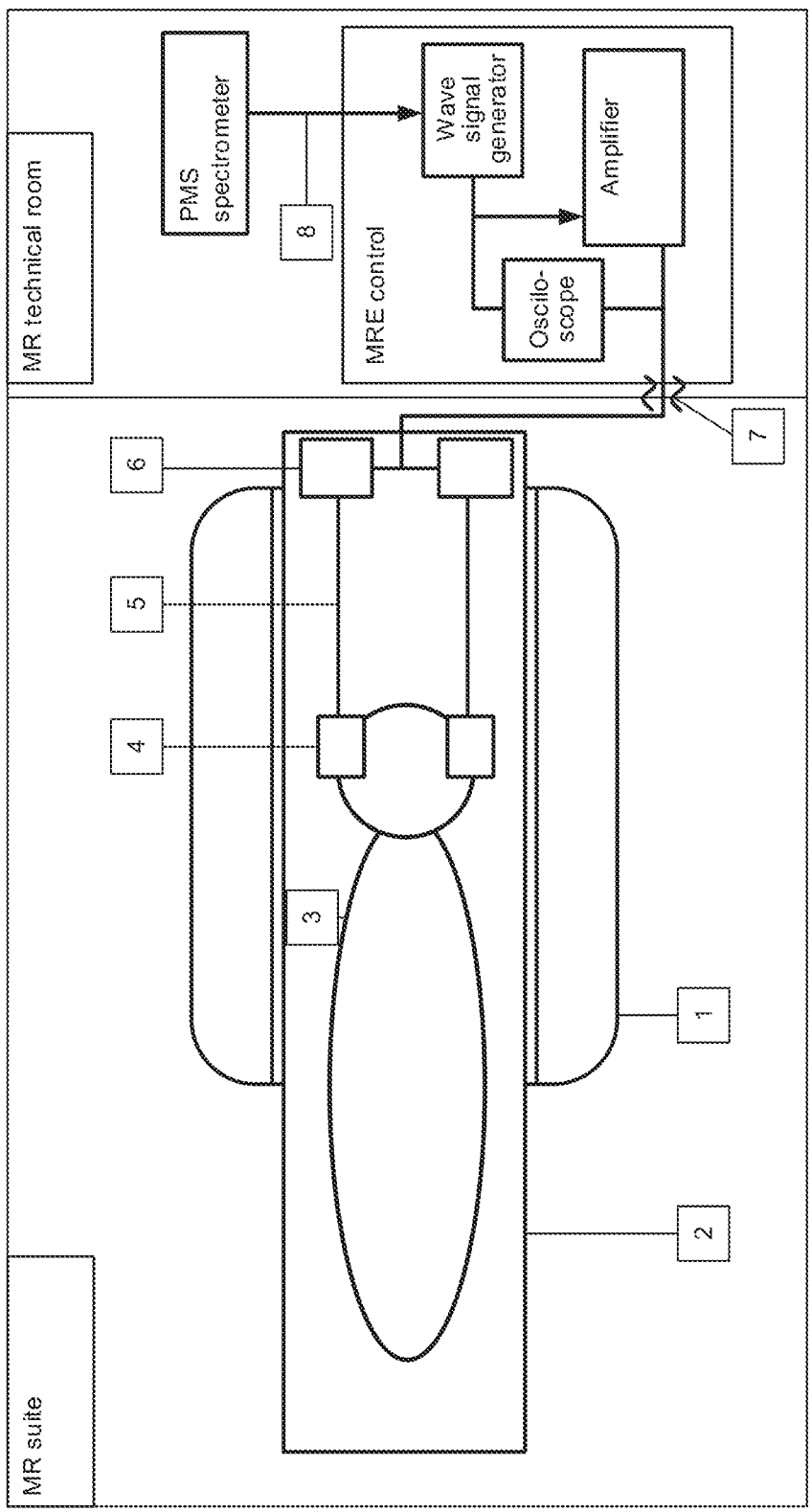
FIG. 7 is a diagram illustrating the operating environment of an embodiment of the invention.

FIG. 6 provides an overview of the operating principle of some embodiments of the invention. The overall setup is shown in FIG. 6(a). Similar to standard MRI brain imaging, the patient is positioned supine on the MRI table with the head inside a commercially available head-coil. The additional MRE setup consists of two parts, one active part positioned at the top end of the MR table, and one passive part mounted to the surface of the head-coil. All elements are MR compatible and hence non-magnetic. Furthermore, the passive element close to the patient is additionally non-conductive in order to avoid any B1-induced local heating effects. Both parts are connected via a flexible nylon and carbon filled push-pull-rod. The active element in this embodiment consists of a non-magnetic coil which is positioned on a first cantilever element (FIG. 6(b)). The coil oscillates mechanically in the feet-head direction (i.e. the direction of the patient axis) due to an applied oscillating current within the presence of the static magnetic field BO of the MRI system (1A, 6VPP, 6 Watts). The mechanical oscillations are transmitted via the flexible nylon and carbon filled push-pull-rod to the passive part. The outer part of the rod, i.e. its outer carbon sheath does not move, but only the nylon interior which is covered and protected. The mechanical oscillations in feet-head direction are transformed in the passive part via a second cantilever element into an oscillation into the left-right direction (FIGS. 6(c) and (d)). This oscillation is coupled via a dome-shaped piston to the skull. A turn-able adjusting knob allows positioning of the piston to the patient-specific distance.

With such an arrangement an MR compatible transducer for MR elastography is obtained that is simple and easy to use, whilst providing repeatable and accurate vibrations and being less obtrusive for imaging subjects. In particular, the flexible connecting rod provides for a greater degree of freedom of the operator in placing the actuator end of the transducer on the subject, whilst the connecting rod mechanism itself is sufficiently longitudinally rigid such that good and accurate transmission of vibrations from the drive element to the actuator end is maintained.

In other embodiments, a different drive mechanism may be used, in place of the cantilevered active element of the above described embodiment. In particular, in one embodiment the passive element positioned near the patient and carrying the oscillator piston is driven by a piezo-electric crystal, provided with a suitable drive signal so as to cause oscillation thereof. In this respect, the piezo-electric crystal may directly drive the passive element, such that the active cantilevered element and the connection rod of the first embodiment are not then required.

In addition, in a further embodiment, instead of a piezo-electric (PE) crystal being used, a photo-mechanical crystal is used instead. Photo mechanical crystals are known in the art as actuators, and operate to change their shape when illuminated by light, and particularly laser light. The shape change is not usually permanent, however, and hence like piezo-electric crystals the photo-mechanical crystal will typically resume its shape very quickly when the illumination is removed. Such behavior therefore leads to oscillatory movement when the crystal is subjected to pulsed illumination, for example by a laser, as the crystal typically bends in the presence of illumination and then straightens when the illumination is removed. This oscillation can be used in a further embodiment to drive the oscillatory movement of the passive element, to cause the photo-mechanical crystal oscillations to be transferred into the patient being imaged. A further advantage of the photo-mechanical crystal arrangement when compared to the piezo-electric arrangement is that the crystal can be fed with light to drive the crystal via an optical fiber, which is typically non-conductive, and hence MR artifacts will be reduced. In contrast, the PE crystal requires conductive wires to be fed to it to provide a drive signal.

Another embodiment of the invention consists of a motor attached to a shaft which transmits the vibration to the front end module to generate a mechanical oscillation at the patient. This motor (1808, 1908) may be MR compatible and sit within the MR room or alternatively may be MR incompatible and reside in the MR control room (see FIGS. 18 and 19). The shaft (1912) may be flexible or inflexible and transmits the motion of the motor by rotation or, in other embodiments by push pull motion (see FIGS. 18 and 19). In any event the shaft transmits the motion to the patient, where it is converted to mechanical oscillation through the use of a special front end designed specifically for each particular region of the body (see FIGS. 18 and 19). The shaft transmits the motion to the front end through direct coupling or through the use of laminar elements, as described in the embodiments discussed previously, and further below.

Figure 20:
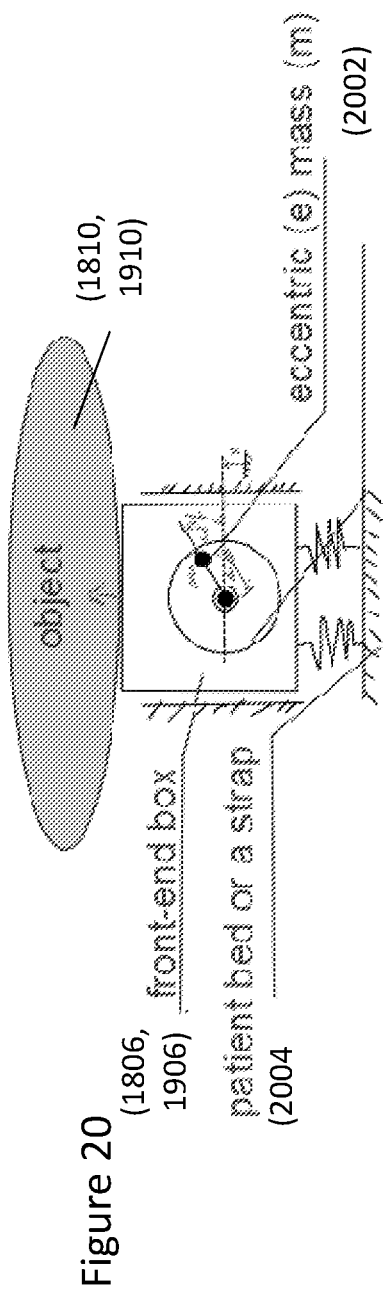
FIGS. 20 and 21 are diagrams of elements used in the sixth and seventh embodiments.
Figure 21:
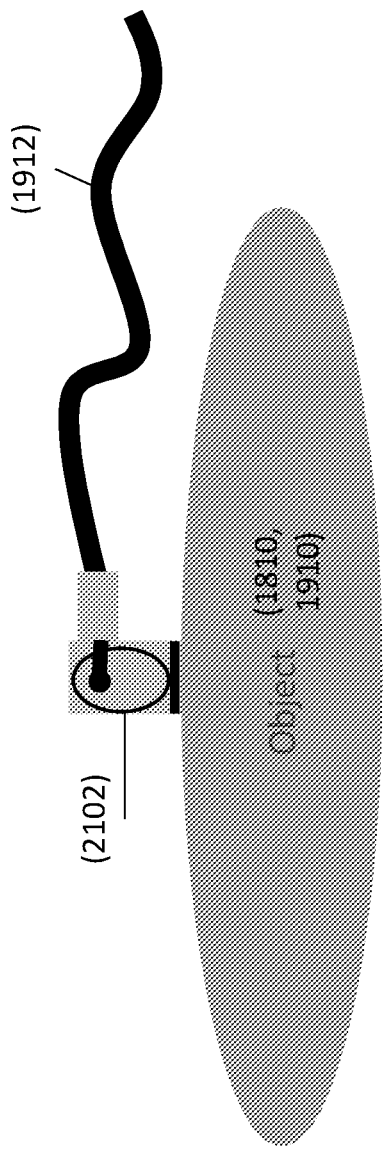

In the front end, the shaft motion may be used to move a cam and/or camshaft mechanism to generate the mechanical oscillation motion (see e.g. FIG. 21). Alternatively, in the front end the shaft motion may be used to move an eccentric rotational mass to generate the mechanical oscillation motion (see e.g. FIG. 20). In either case the front end may or may not be secured onto the patient.

DETAILED DESCRIPTION OF EMBODIMENTS

Figure 1:
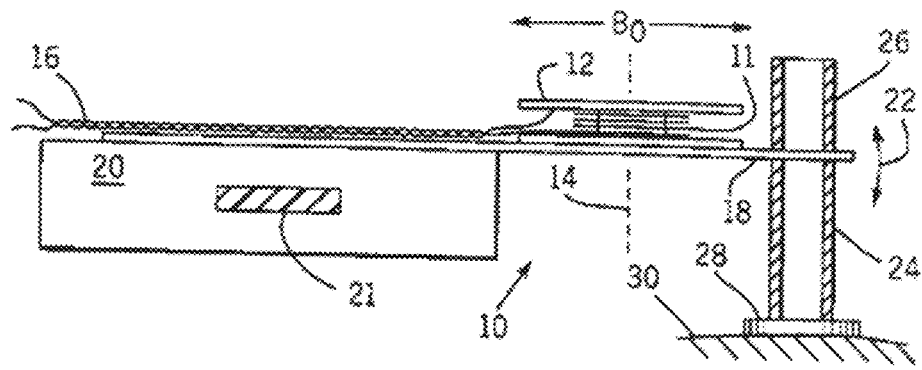
FIGS. 1 to 4 are various prior art images of related prior art arrangement.
Figure 2:
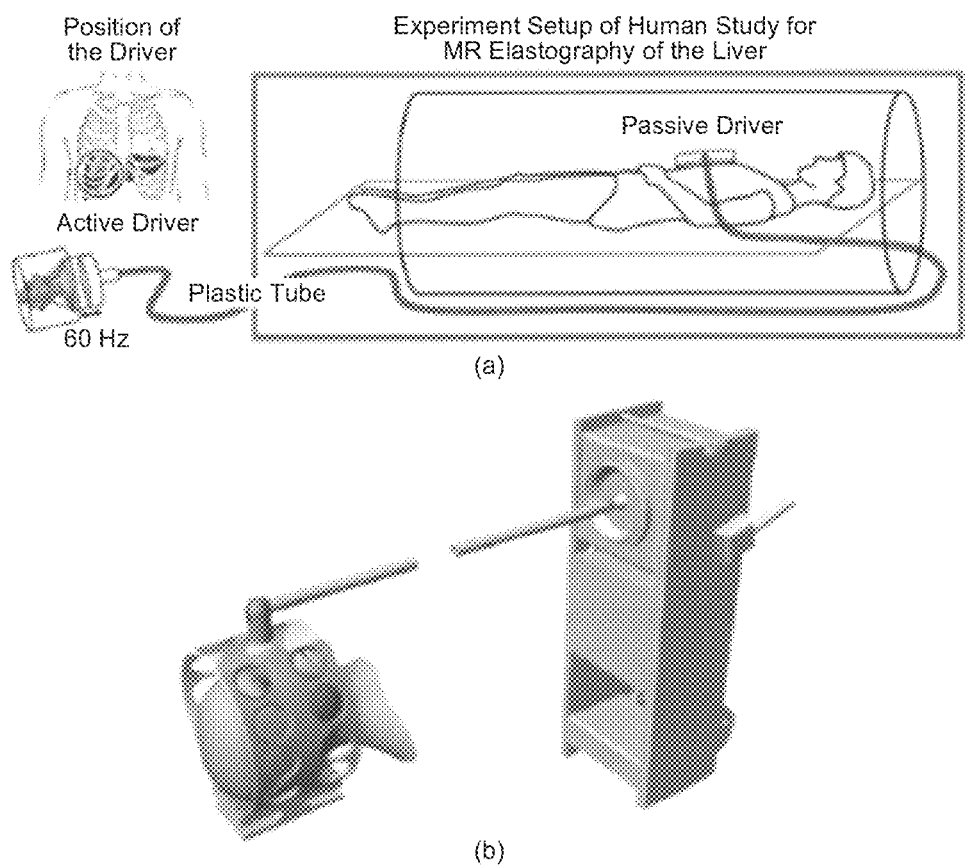
Figure 3:
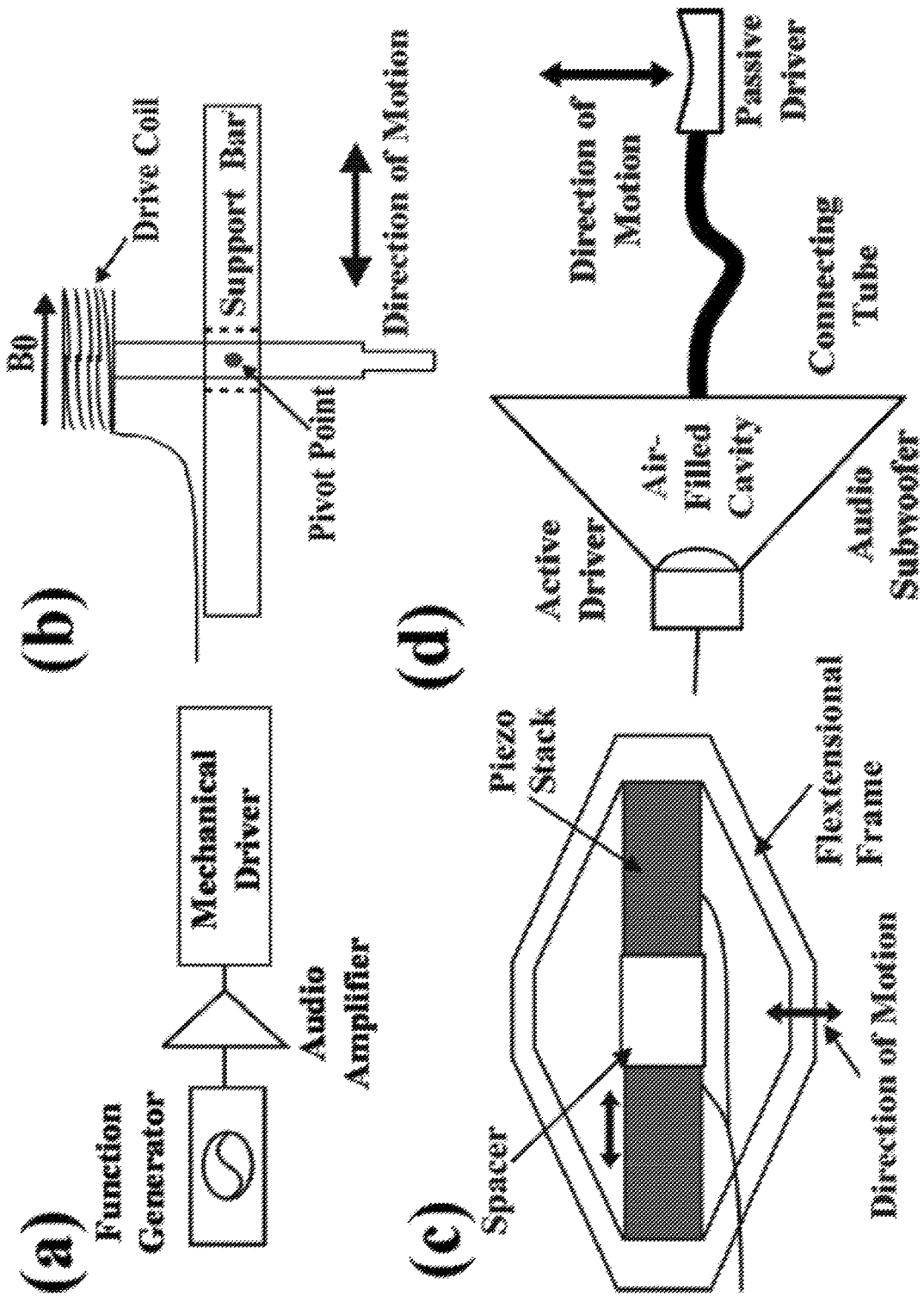
Figure 4:
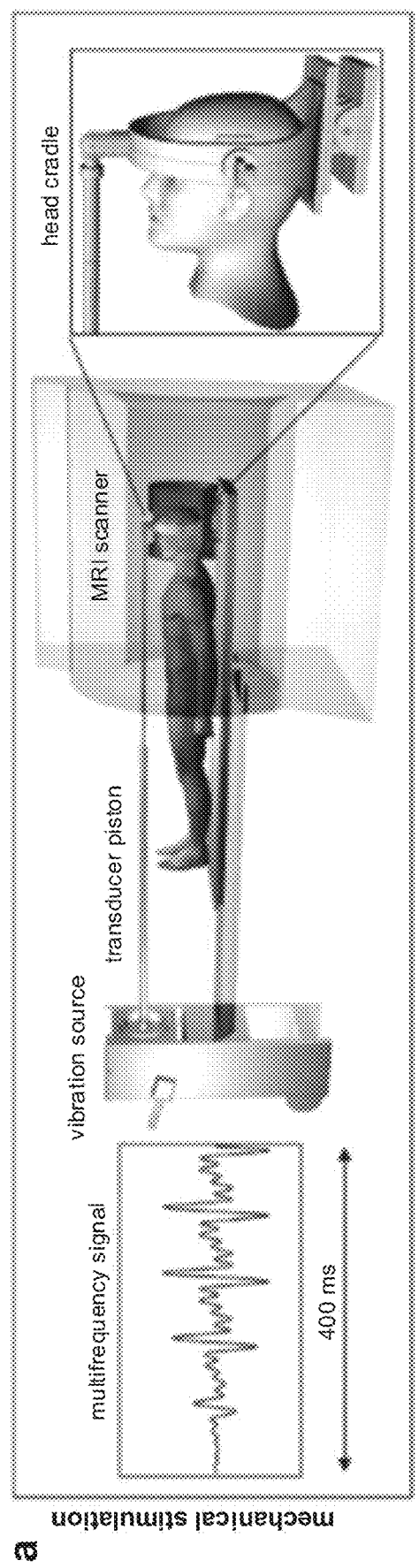
Figure 5:
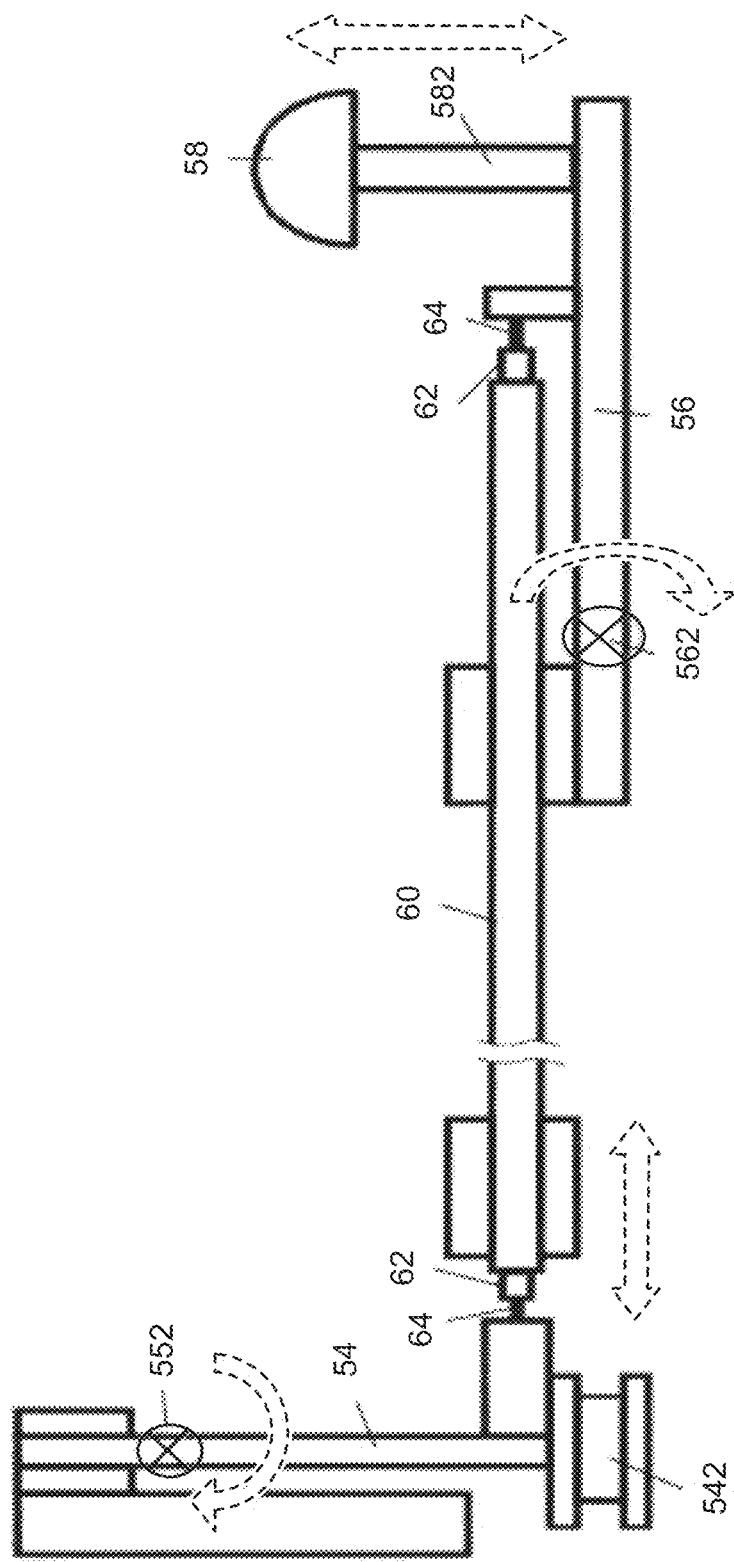
FIG. 5 is a diagram of a first embodiment of the invention.
Figure 8:
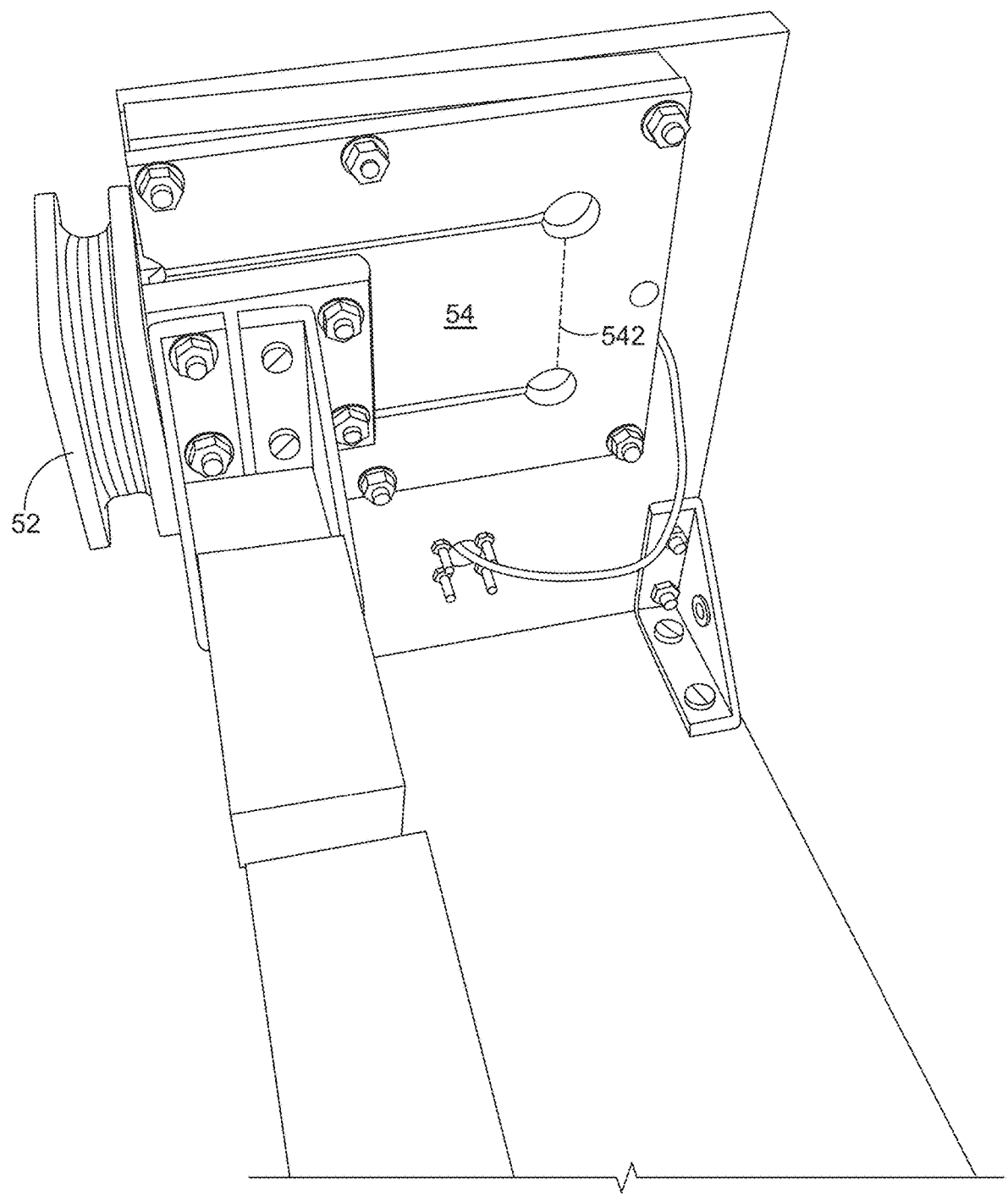
FIGS. 8 to 10 are photographs of various elements of the first embodiment of the invention.
Figure 10:
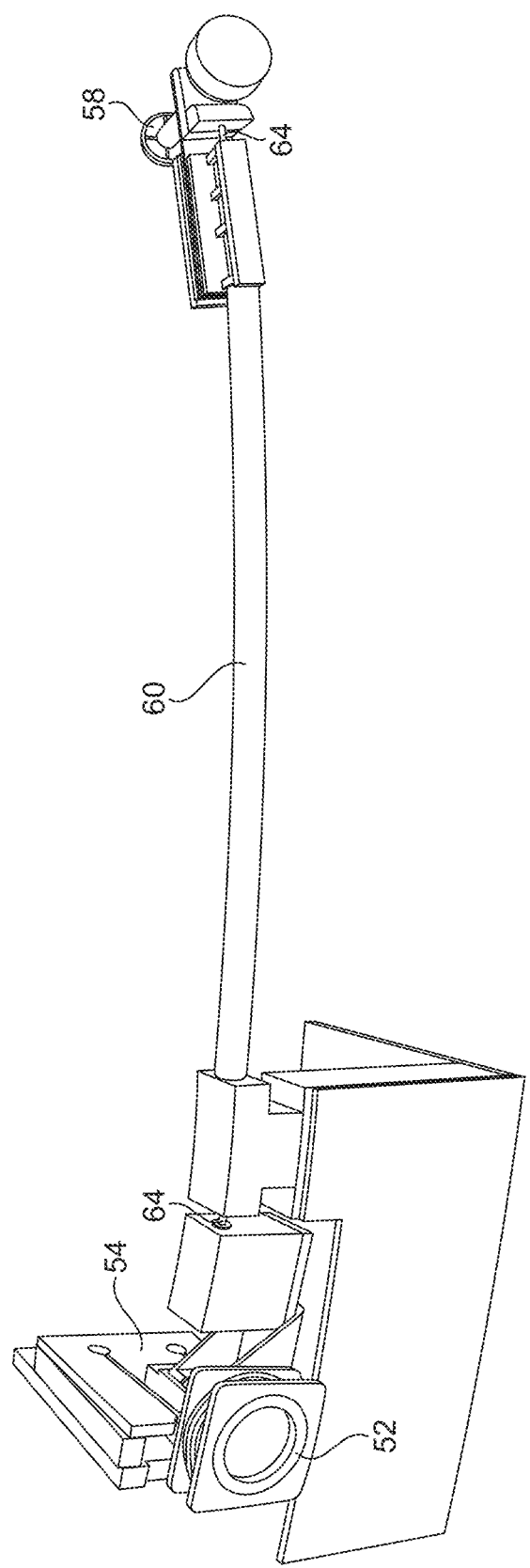

A first embodiment of the invention will now be described with respect to FIG. 5 to FIG. 5 is a schematic diagram of the first embodiment. Here, a cantilever element 54, fastened at one end 542 so as to reciprocally pivot thereabout, is provided, having mounted on the free end thereof a conductive coil 542. The cantilever element 54 is made from a flexible high-density plastic material, such as PEEK. The coil 52, shown in more detail in FIGS. 6(b), 8, and 10 is formed of non-magnetic conductive wire and is mounted on the cantilever element 54 so that the plane of the coil is transverse to the plane of the cantilever element 54, with the axis of the coil aligned to and extending along the major plane of the cantilever element 54. The arrangement of the coil and the cantilever element 54 is such that when the coil 52 is placed within the BO field of an MRI scanner, and an alternating current fed therethrough, the coil is caused to move reciprocally under the influence of the BO field. Because the coil is affixed to the cantilever element 54, the cantilever element is caused by the coil to reciprocally rotate back and forth about pivot point 552. Collectively, therefore, the coil 542 and cantilever element 54 form a cantilever driver.

The cantilever element 54 has mounted thereon next to a coil a block portion, which provides an abutment surface to which is fastened a short, cylinder-like, flexible element 64. Flexible element 64 is substantially non-compressible along its long axis, but is sufficiently flexible so as to allow it to be bent slightly in directions orthogonal to the long axis, i.e. such that one end thereof deflects away from the long axis. As noted, a proximal end of the flexible element 64 is fastened e.g. by glue to the block portion connected to the cantilever element 54, with the distal end of the flexible element 64 being connected to a flexible connecting rod 62. The flexible connecting rod is substantially non-compressible along its long axis, but flexible in directions orthogonal to the long axis, such that it can be curved away from the at-rest long axis along its length. The flexible connecting rod 62 slides within a flexible connecting tube 60, and is adapted so as to have a low sliding friction to enable easy transfer of vibrations from the cantilever driver. Example components that can form the connecting rod 62 and connecting tube 60 are, for example, the Sullivan Gold-N-Rod Push-Pull and Pull-Pull Control Rods, available from Sullivan Products, Baltimore, Maryland.

Figure 9:
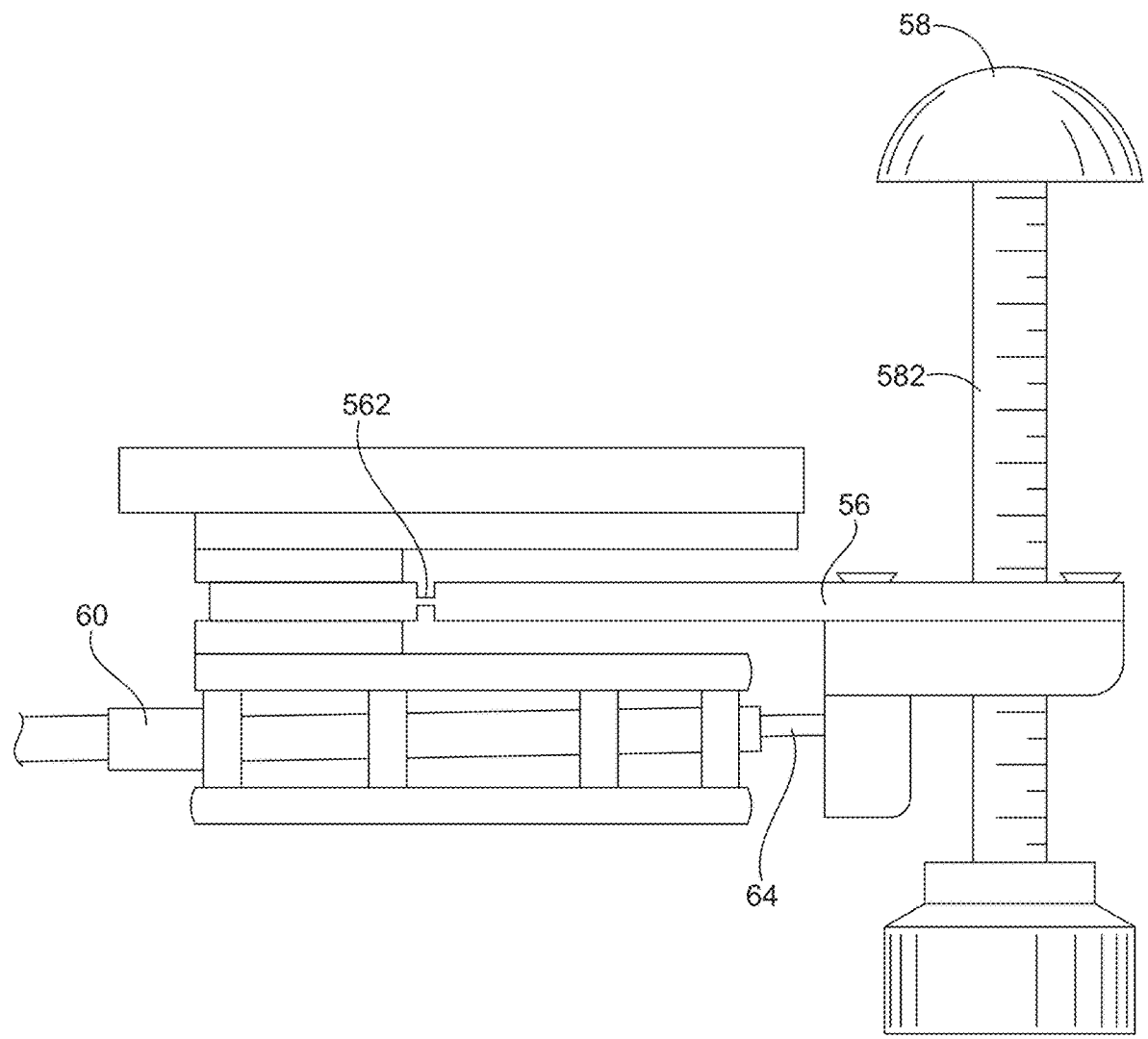

Fastened at the distal end of the connecting tube is a second cantilever element, in the form of driven cantilever 56, as shown in FIGS. 5 and 9. Again, driven cantilever 56 is formed from a dense plastic type material, such as PEEK, and the cantilever is arranged to pivot about a fixed pivot point 562 arranged at the fixed end thereof, fastened to the outer surface of the connecting tube 60. At the free end of the cantilever is provided an adjustable piston 58, comprising a screw threaded shaft extending orthogonally to the plane of the driven cantilever 56, having at the distal end thereof a dome structure, for example of rubber or rubber like material, which in use contacts the body of the subject to transmit vibrations into the body at the contact point. The piston 58 is adjustable by virtue of the screw thread so as to alter the height of the dome structure with respect to the cantilever, to allow for easy adjustment to individual subjects.

The distal end of the connecting rod 62 is also provided with a short, cylinder-like, flexible element 64. As before, the flexible element 64 is substantially non-compressible along its long axis, but is sufficiently flexible so as to allow it to be bent slightly in directions orthogonal to the long axis, i.e. such that one end thereof deflects away from the long axis. The proximal end of the element 64 is fastened to the distal end of the connecting rod, whereas the distal end of the element 64 is fastened e.g. by glue to a second block portion that is affixed to the driven cantilever element 56.

The operation of the above arrangement is as follows. Firstly the arrangement is placed with respect to the subject to be imaged, such that the driven cantilever element with the adjustable piston 58 is placed proximal to the subject, with the dome structure of the piston contacting the subject where it is desired for the vibrations to be produced, i.e. on that part of the subject's anatomy that is to be imaged using MRE techniques. The driven cantilever element is then secure in position with respect to subject e.g. by fastening to a head clamp or the like. The proximal end of the arrangement with the cantilever driver is then positioned at the top end of the MR table, away from the MR bore, so as to try and minimize imaging artifacts.

Once the subject is in position and MRE imaging is to commence, an AC current is fed to the coil 542, at the same frequency as the desired frequency of vibrations. When the MR scanner is activated the BO field of the scanner causes the coil to reciprocally oscillate, as discussed above, and as known, for example, from U.S. Pat. No. 5,952,828. Due to the mounting of the coil on the end of the cantilever driver structure 54, the cantilever driver structure 54 is caused to reciprocally rotate backwards and forwards about its fastening point in an oscillating manner. This reciprocal rotational oscillation is transformed into a reciprocal linear oscillation of the connecting rod 62 within the connecting tube 60 via the short flexible element 64 that is connected to the cantilever driver and the proximal end of the connecting rod 62. This proximal flexible joint which is otherwise rigidly connected to the cantilever driver and the connecting rod in combination with the longitudinal stiffness but lateral bendability of the connecting rod contributes to a very low loss transmission of the cantilever driver vibrations through the connecting rod to the driven cantilever arrangement. Here, the reciprocal linear motion of the connecting rod within the connecting tube is then converted back, via the distal flexible joint 64 at the distal end of the connecting rod 62, to a reciprocal rotational oscillation of the driven cantilever 56 about axis 562. This causes the adjustable piston 582 with the dome structure 58 to oscillate up and down against the body of the imaging subject, thus transmitting controllable and repeatable vibrations into the subject, for MR elastography imaging purposes.

The present embodiment provides numerous advantages over the prior art arrangements. Firstly, the use of an electro-sensitized coil as a driver provides stable and "clean" mechanical vibrations, thus improving image quality. In addition, there are no electromagnetic components in the vicinity of the patient, and hence the patient's safety is improved, as the electromagnetic component can be positioned either to the top or bottom of the MR bore (behind the head, or at the feet). In addition, the presence of a non-shielded electromagnetic component would normally introduce significant distortion of an MR signal, therefore removing the electro-sensitized component from the scanned region as in the present embodiment hence provides a significant improvement of signal quality.

Moreover, in the present embodiment the oscillation motion is translated into uni-axial motion via a flexible element. This gives assured stability and precision of the oscillations as no mechanical moving part is required to translate the motion. Furthermore, using a semi-flexible rod to translate motion from the driver to the (patient) front-end allows for patient-specific positioning. Additionally, the translation of longitudinal motion into lateral motion by a flexible element provides for lossless translation of signal from the driver to the patient. As a consequence of all these advantages a wide range in flexibility in designing a patient friendly system for a variety of different MRE imaging applications (breast, cardiac, liver, kidney . . . ) is obtained.

Figure 13:
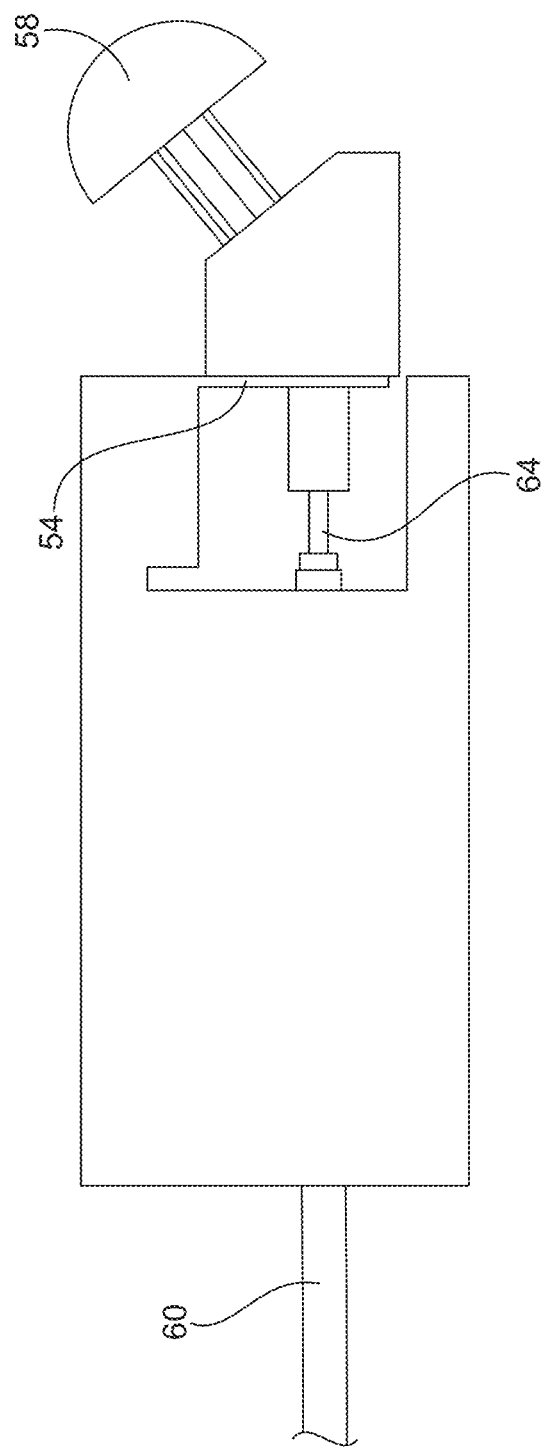
FIG. 13 is a photograph of an element of a fourth embodiment of the invention.
Figure 14:
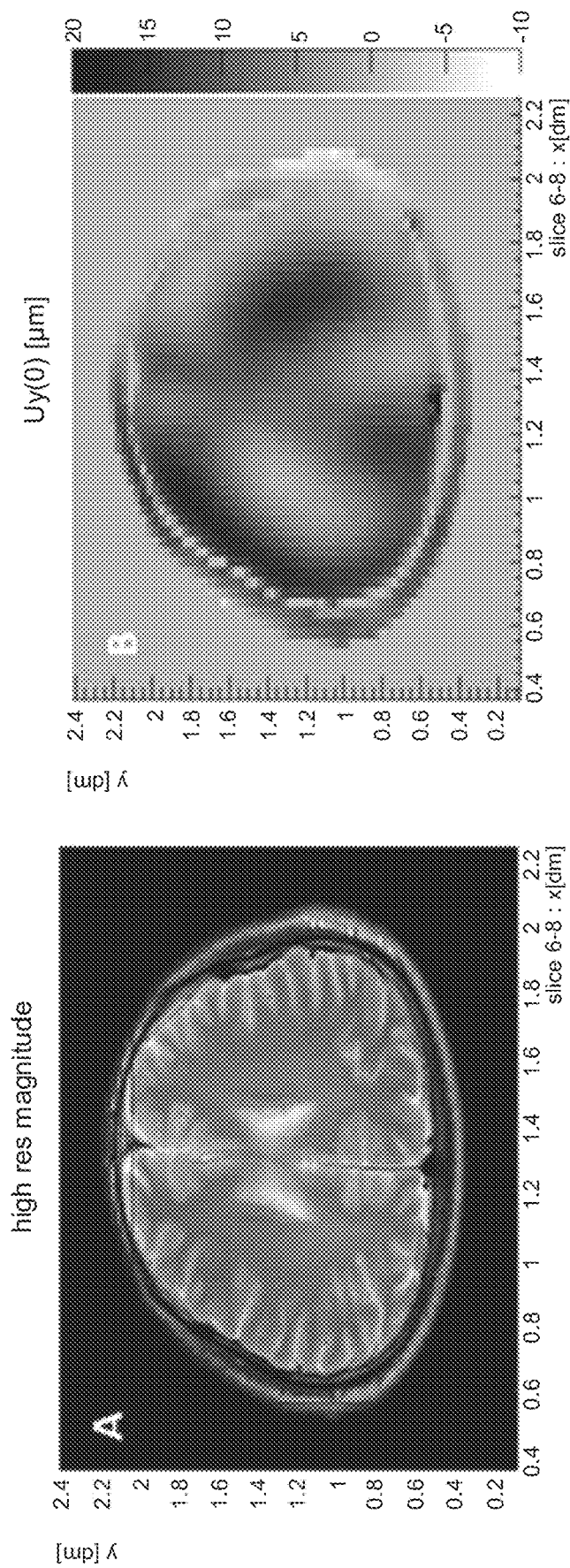
FIGS. 14(a) to (d) are various brain scans of a healthy subject illustrating the results that can be obtained using an embodiment of the invention.
Figure 14:
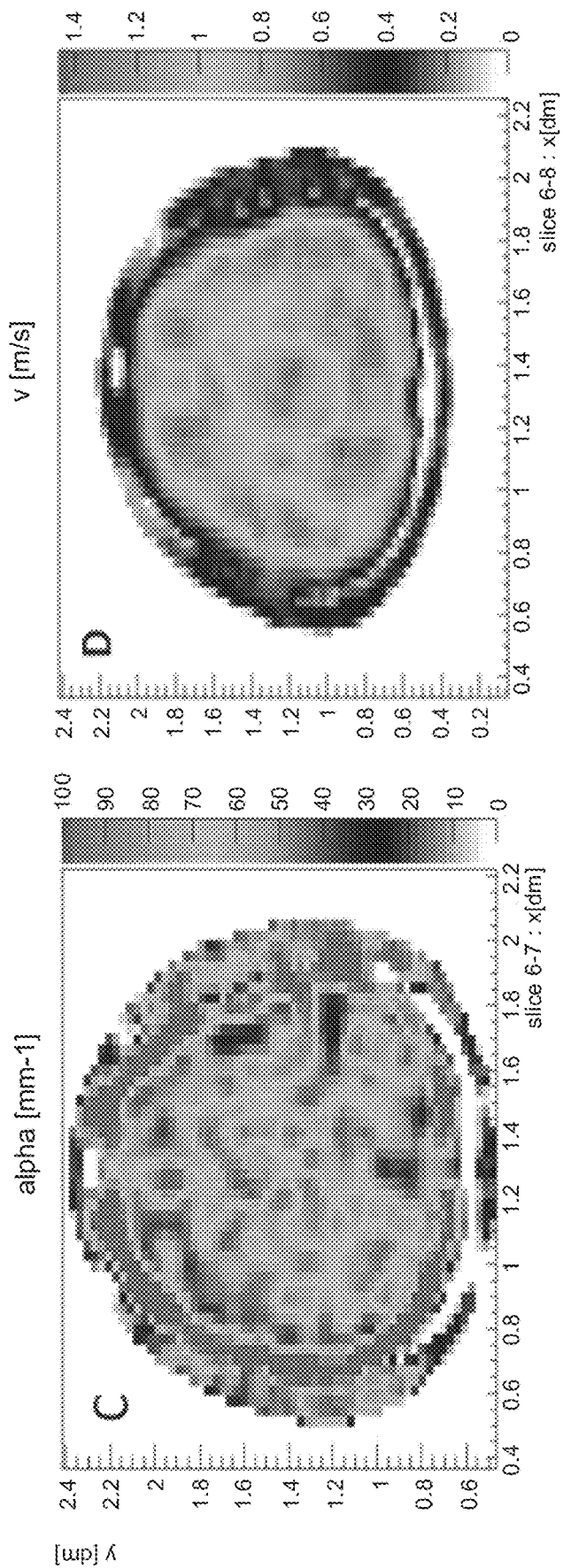

FIG. 13 illustrates some images of brain scans showing the effects of the arrangement of the first embodiment when in use. Here, the magnetic resonance actuator of the first embodiment has been tested on multiple healthy subjects. Here, brain tissue (high resolution anatomy scan depicted in A) has been perturbed using a low frequency (28 Hz), low amplitude vibration (visible in B), while providing spatial viscosity information (in C) along a full wave-speed map (in D, directly related to tissue stiffness).

Various modifications may be made to the above described embodiment to provide further embodiments. For example, it is not necessary that the piston 582 extend from the driven cantilever structure orthogonally, and in other embodiments it may extend at any angle therefrom, particularly an acute angle. FIG. 13 illustrates an arrangement where the piston 582 extends from the cantilever structure at a substantially 45 degree angle. In addition, in the arrangement of FIG. 13, the driven cantilever structure itself has been re-arranged, such that the major plane of the cantilever extends substantially orthogonal to the direction of the connecting rod, and the flexible element 64 acts directly on the major plane of the cantilever structure. Such arrangement helps provide for alternative driven tools, for use in accessing different parts of a subject to be imaged.

Figure 11:
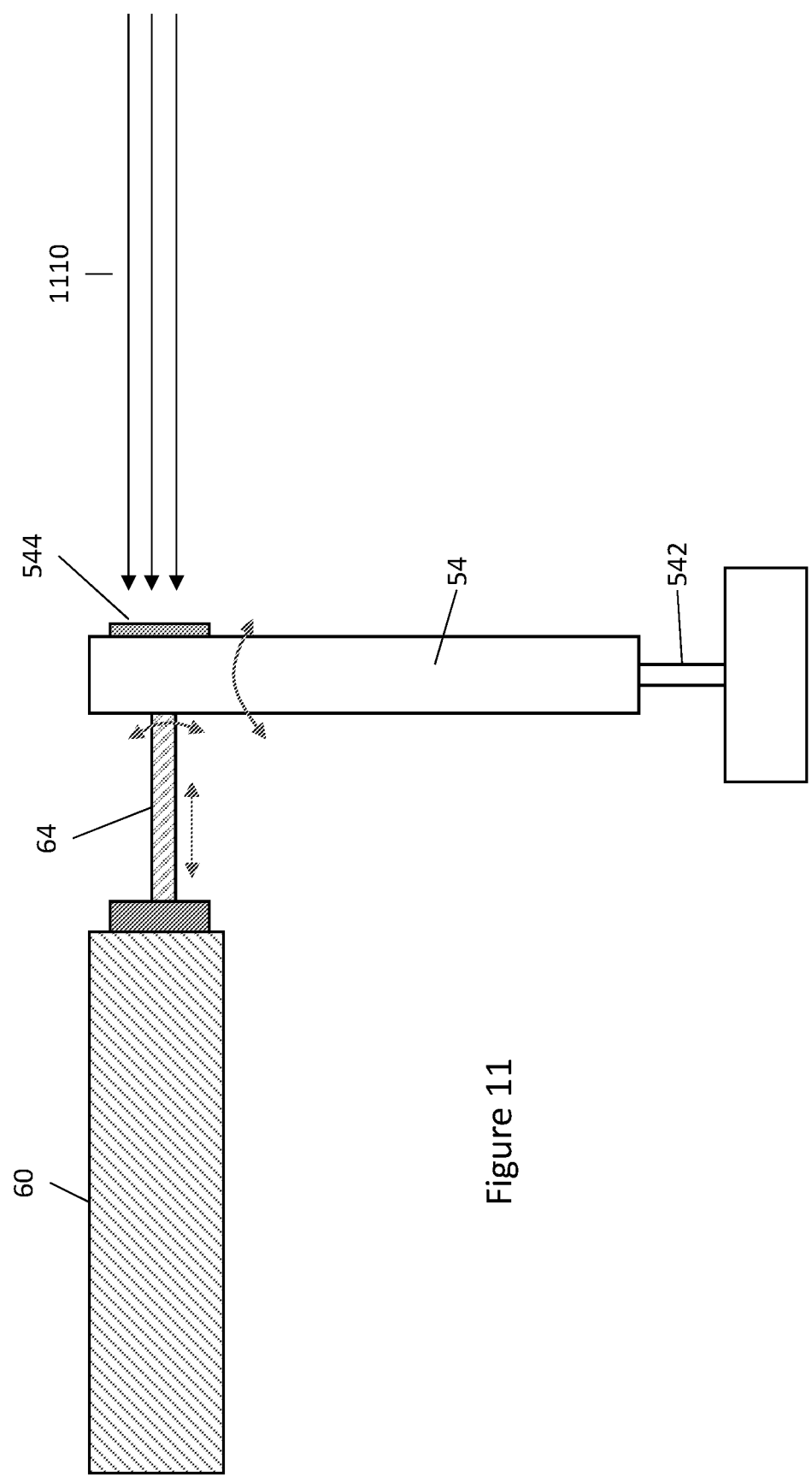
FIG. 11 is a diagram of a second embodiment of the invention.
Figure 12:
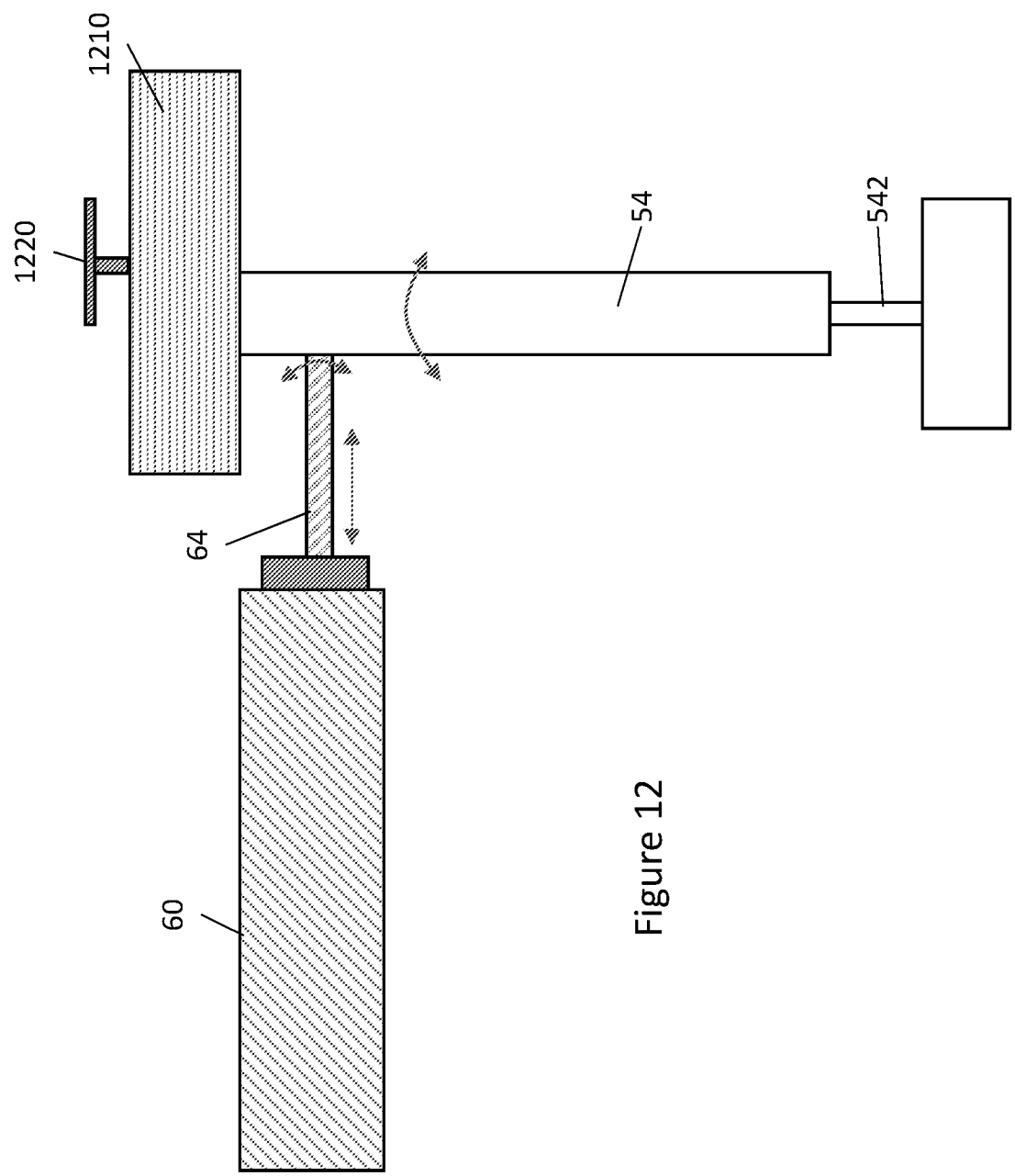
FIG. 12 is a diagram of a third embodiment of the invention.

FIGS. 11 and 12 illustrate alternative embodiments, which make use of different motive arrangement for the cantilever driver element other than the coil and the BO field. For example, in the embodiment of FIG. 11, instead of having the coil mounted at the end of the cantilever driver element 54, the element is provided on its opposite face to that which makes contact with connection element 64 a darkened target area 544, which is used as a target area for a laser pulse 1110. The laser pulse 1110 strikes the darkened target area 544, which absorbs the energy of the photons in the pulse, converting the momentum of the photons into movement of the cantilever driver element (as well as heating up the target area). The pulses may be repeated at high frequency to push the end of the cantilever to a desired oscillation amplitude position, and then stopped for a period to allow the cantilever to spring back the other way. Once the cantilever has sprung back as far as it will in the opposite direction, the high frequency pulses can then commence again to push the cantilever back in the first direction until the desired oscillation amplitude position is reached again. This cycle can then be repeated as many times as required to maintain the oscillation of the cantilever.

The advantage of using a laser is that it can be accurately directed onto a small target from a safe distance away, and hence the laser may be kept well away from the MR bore, thus meaning that there are no conductive elements near the bore which may cause image artifacts.

FIG. 12 shows an alternative embodiment, which makes use of a clockwork mechanism 1210 as a motive element for the cantilever driver 54. Here, as shown, a clockwork mechanism, preferably formed completely of plastic parts, or predominantly of plastic parts with a non-magnetic winding spring, is provided mounted on the end of the drive cantilever 54. The clockwork mechanism may drive an eccentrically mounted weight, or else the clockwork mechanism itself may be eccentrically mounted on the end of the cantilever 54 (as shown), in either case to cause a reciprocating bending force to be applied to the top of the cantilever 54, so as to make it reciprocally rotationally oscillate from side to side. In use, therefore, the clockwork mechanism 1210 would be wound by handle 1220, and then released to start the oscillations, which in turn drive the rest of the mechanism in the same way as described previously in respect of the first embodiment.

The advantage of using a clockwork mechanism again lies in MR safety and reduction in image artefacts, in that the amount of conductive material to be placed near the bore of the MR scanner can then be further reduced.

Figure 16:
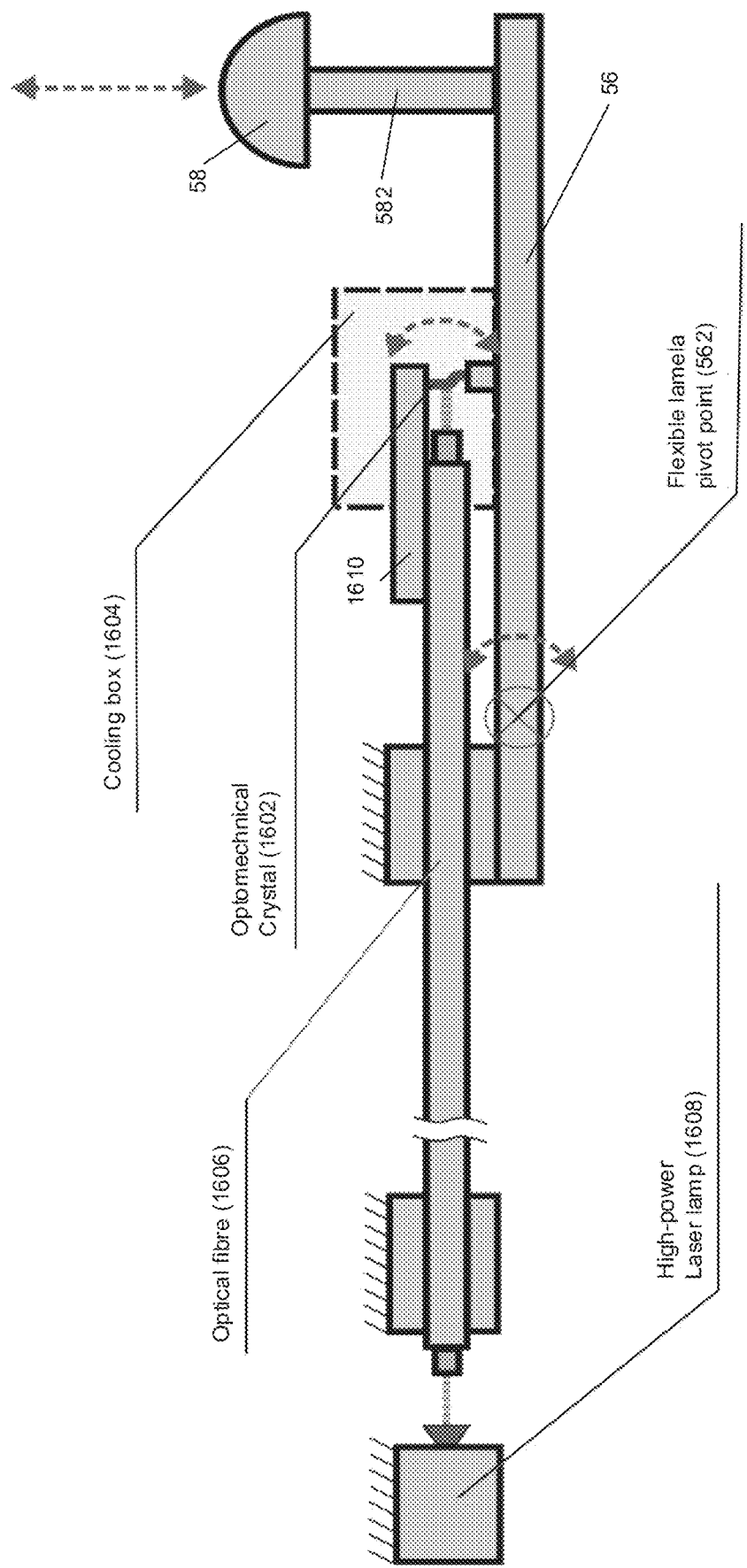
FIG. 16 is a diagram of a fourth embodiment of the invention.
Figure 17:
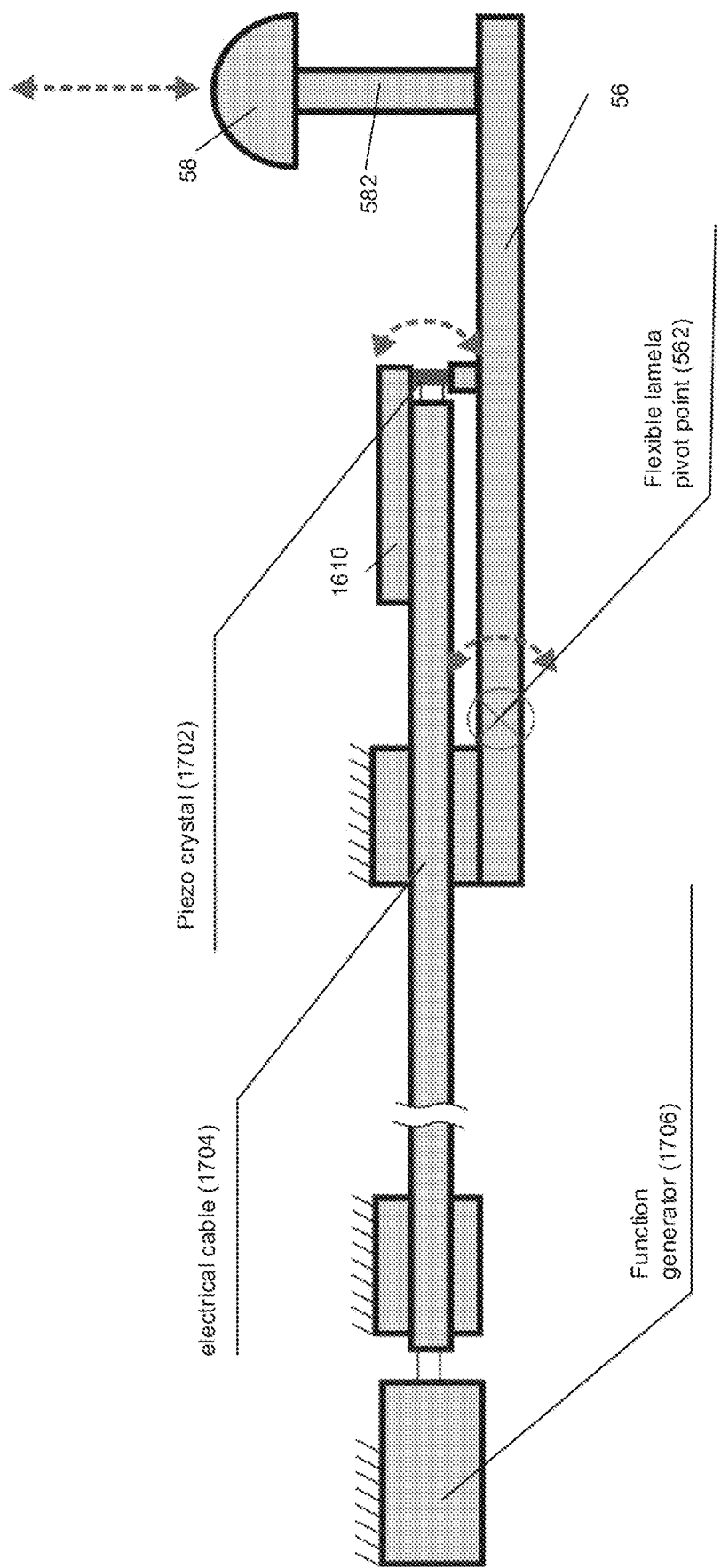
FIG. 17 is a diagram of a fifth embodiment of the invention.

FIGS. 16 and 17 illustrate further embodiments, which do not include the cantilever driver element or the connecting rod, and instead have the cantilever driven element driven directly by a crystal that provides an oscillatory motive force. The crystal may either by a photo-mechanical (opto-mechanical) crystal, driven by a light source such as a laser, or a piezo-electric crystal driven by an applied electric field.

Turning to FIG. 16 first, here the driven cantilever element 56 is provided, which is anchored at one end and freely extending at the other such that it oscillates about the pivot point 562. Also, as before, piston 582 mounting dome structure 58 thereon to contact the subject in use are also provided, extending from the free end of the driven cantilever element 56.

In order to drive the cantilever element to oscillate, an opto-mechanical crystal 1602 is provided, with a cooling box 1604. The opto-mechanical crystal 1602 is mounted between the driven cantilever 56, and a fixed surface, so that in use the crystal moves against the fixed surface so as to exert a motive force on the cantilever 56, thus causing the cantilever to move. As shown, the crystal 56 is mounted substantially half way along the cantilever 56, such that small movement of the crystal is amplified by the length of the cantilever to provide a larger movement at the free end of the cantilever.

In order to drive the arrangement an optical fiber 1606 is provided, coupled to a light source 1608, such as a high powered laser lamp. The optical fiber 1606 guides light from the light source 1608 therealong, and outputs the light in use such that it is then incident on the opto-mechanical crystal.

The light source 1608 is able to produce light of different wavelengths, from UV light through the visible spectrum to IR light, and is further able to produce ranges of wavelengths of light at the same time, i.e. it can be a broadband source as well as being narrowband. Such performance can be obtained by having lasers of different wavelengths that are mixed together, or by having a broadband optical source such as a lamp and then applying the necessary filters. Other arrangements for producing different wavelengths of light for illumination will be apparent to the intended reader, and embodiments of the invention may use any such arrangements.

The opto-mechanical crystal, which is generally of an elongate shape, such as in the form of an elongate strip or thread, has its ends secured between the fixed surface and the cantilever. When illuminated by light of a first wavelength or range of wavelengths, for example shorter wavelengths such as UV light generated by the light source 1608, the crystal will try to bend or otherwise deform, thus effectively shortening the distance between the fixed surface and cantilever, and moving the cantilever upwards towards the fixed surface. However, when the illumination wavelength is changed, for example to lengthen the illuminating wavelength further into the visible light spectrum or towards the infra-red, the crystal will return to its normal shape, thus allowing the cantilever to return to the original position. Hence, by repeatedly controlling the illumination of the crystal by the light source, and in particular by controlling the illumination wavelength and/or intensity, the crystal can be made to repeatedly oscillate between the two positions, thus also oscillating the driven cantilever element 56.

As noted above, one advantage of the above arrangement is that the crystal is fed the illuminating light via an optical fiber, which increases MR safety and image quality as no conductors are then needed near the subject.

FIG. 17 illustrates an alternative embodiment, which is substantially identical to the embodiment of FIG. 16, but instead of using an opto-mechanical crystal a piezo-crystal 1702 is used, secured between the fixed surface 1610 and the driven cantilever 56. The piezo-electric crystal is typically of an elongate shape when at rest, and then deforms so as to effectively shorten the distance between its ends when under an applied electric field, thus moving the cantilever to which it is affixed towards the fixed surface 1610. The piezo-crystal 1702 is fed with an electrical current to generate an electrical field across the crystal by electrical cable 1704, which receives an oscillating electrical signal from function generator 1706. In use, therefore, the oscillating electrical signal causes the piezo-electric crystal to pull the cantilever 56 up towards the fixed surface 1610, and then to release the cantilever repeatedly, to thereby cause the cantilever to oscillate. The oscillations are then transmitted via the dome structure 59 to the subject to be imaged, as described previously.

Piezo-electric crystal technology is well developed, and PE crystals are available that produce a high force such that strong and repeatable vibrations can be obtained. One drawback of using the piezo electric crystal arrangement shown, however, is that the conductive cable is required to supply current to the crystal, and hence there is the possibility that the cable may cause imaging artefacts. However, these are anticipated to be minor. One prior art example of using PE actuators in MR studies is Gizewski et al *Cerbral actovation using a MR-compatible piezoelectric actuator with adjustable vibration frequencies and in vivo wave propagation control* NeuroImage vol 24. pp 723-730, 2005.

Regarding the opto-mechanical (photo-mechanical) crystal used in the embodiment of FIG. 16, numerous photoirradiation driven materials are known in the art, such as liquid crystal elastomers, liquid crystal polymers, and diarylethene derivative crystals. Terao et al. in *Light-Driven Molecular-Crystal Actuators: Rapid and Reversible Bending of Rodlike Mixed Crystals of Diarylethene Derivatives Angew*. Chem. vol 124, pp. 925-928, 2012 described a diarylethene derivative rod-like crystal that was able to sustain repeated bending in all directions, and exert similar forces to piezo-electric crystals. Additional information on liquid crystal polymer materials that may also be used are given in White et al. *A high frequency photodriven polymer oscillator* Soft Matter, vol 4, pp. 1796-1798, (2008), as well as in Koerner et al *Photogenerating work from polymers* Materials Today, vol 11, no 79, pp. 34-42, July 2008, and Ohm et al. *Applications of Liquid Crystalling Elastomers*, Adv Polym Sci v. 250, pp. 49-94 (2012). Any information from any of the above references required to understand the structure, arrangement, and operation of the photo-mechanical crystal of the embodiment of FIG. 16 of the present invention is hereby incorporated herein by reference.

Figure 15:
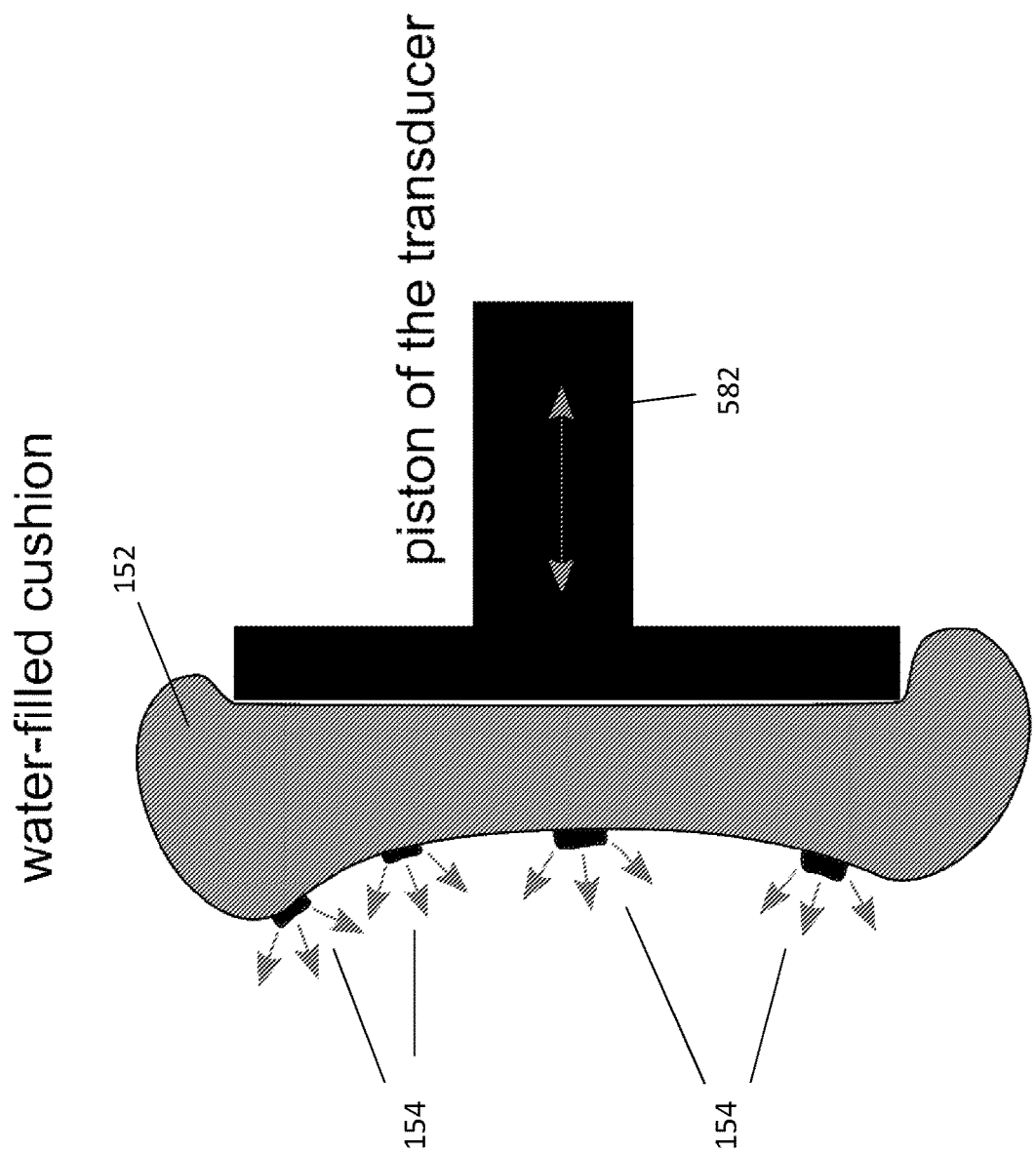
FIG. 15 is a diagram of a water filled cushion that may optionally be used in any embodiment of the invention.

Turning now to FIG. 15, FIG. 15 illustrates an alternative to dome structure 58, which may be used within any of the embodiments described above. Here, dome structure 58 is replaced with a water-filled cushion 152. The water-filled cushion 152 increases patient comfort without losing the desired mechanical wave (due to the fluid-dynamics principle and wave propagation in incompressible fluid). The water filled cushion is optionally provided with a plurality of non-compressible studs on the outer surface that contacts the subject. The studs are preferably equidistantly arranged over the surface, although other arrangements are possible. The studs induce more shear waves compared to a smooth surface, where a predominantly compressional wave could be observed. In other embodiments, other liquids or fluids other than water may be used, provided that they are incompressible such that they transmit the generated vibrations to the subject.

Further embodiments will now be described with respect to FIGS. 18 and 19. In particular, the further embodiments are based upon the arrangement shown in FIG. 19, wherein a front end rotational actuator box provides controlled vibrations, under the control of a rotational shaft, which is flexible, and which links the front end box to a motor, located outside the MR room.

Figure 18:
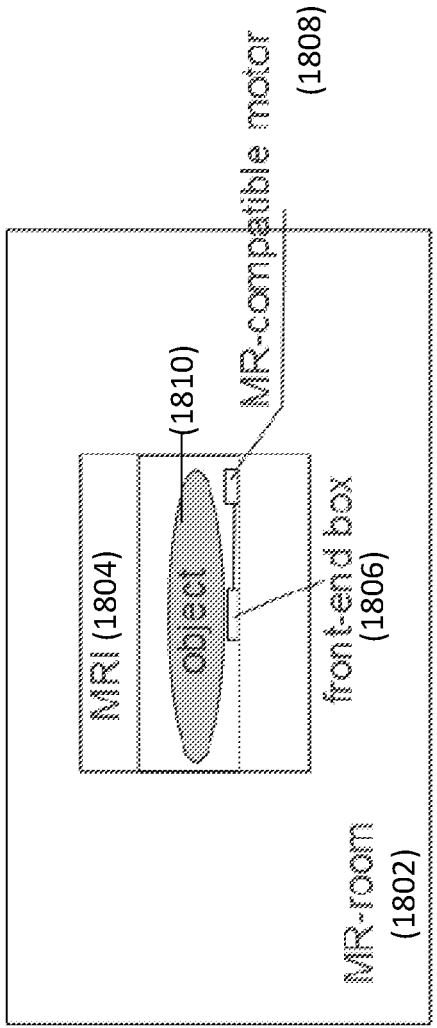
FIG. 18 is a diagram of a sixth embodiment of the invention.

Referring first to FIG. 18, however, FIG. 18 shows one embodiment, wherein a front end box 1806 is located in the bore of an MR imager 1804, in physical contact with an object 1810, such as a patient, which the front end box is to excite with vibrations. The front end box 1806 comprises a vibrating element which produces controlled vibrations, which are passed to the object 1810 which is to be imaged. The front end box 1806 produces any vibrations under the power of an MR compatible motor 1808, contained within the bore of the magnetic resonance imager. In such a case, the motor and the front end vibrator box 1806 are contained within the MR room 1802, and is shown within the bore of the magnetic resonance imaging machine 1804.

Figure 19:
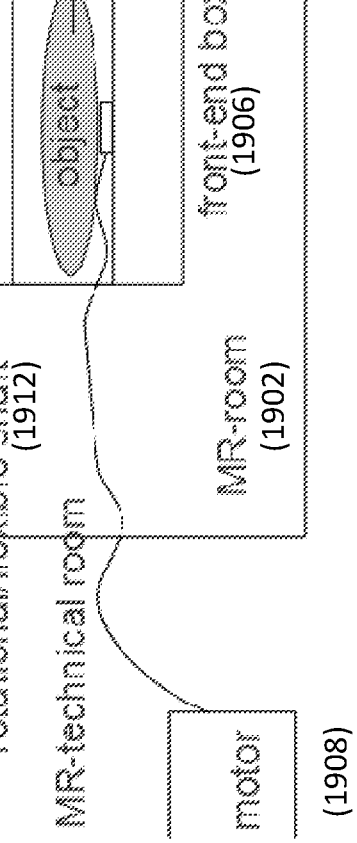
FIG. 19 is a diagram of a seventh embodiment of the invention.

Of more interest, however, is the embodiment shown in FIG. 19. Here, a front end vibrator box 1906 is located within the bore of the MR imager 1904, in physical contact with the object of the image 1910. The front end vibrator box 1906 is attached to a motor 1908, via a flexible rotating shaft 1912, which connects the front end vibrator box 1906 to the motor 1908, which is located in the MR technical room i.e. outside the MR room itself. This arrangement does not require an MR compatible motor to be used as a rotational drive. The flexible rotating shaft 1912 can be an off the shelf component having a fixed outer layer made of a flexible tube, within which is contained a flexible MR compatible rotatable shaft. For example, the flexible MR compatible rotatable shaft is made of phosphor bronze, being an MR compatible material. The phosphor bronze flexible shaft is connected at one end and is driven by the motor 1908, and at its other end to elements within the front end vibrator box 1906, to be described with respect to FIG. 20.

FIG. 20 therefore shows an example front end vibrator box 1806, 1906. It contains a rotationally mounted eccentric mass 2002, which is mounted such that its axle is driven by the flexible rotating shaft 1912, optionally via some gears. The rotation of the flexible shaft 1912 to drive the rotationally mounted eccentric mass causes the rotation of the mass, which due to the eccentric weight distribution across the mass causes vibrations of the front end vibrator box 1806, 1906. Because the front end vibrator box is in contact with the object 1810, 1910, the vibrations are transmitted from the front end vibrator box to the object 1810, 1910.

FIG. 21 illustrates an alternative example, wherein instead of an eccentric mass which is axially mounted centrally, and has a weight distribution which is eccentric, an eccentrically mounted mass, such as a cam shape, or the like, is used as the rotationally mounted mass, the rotation of which, driven by the flexible rotational shaft 1912, causes vibrations of the front end box, which are then transmitted into the object 1810, 1910. FIG. 21 therefore illustrates an alternative embodiment of a front end box to that shown in FIG. 20.

Figure 22:
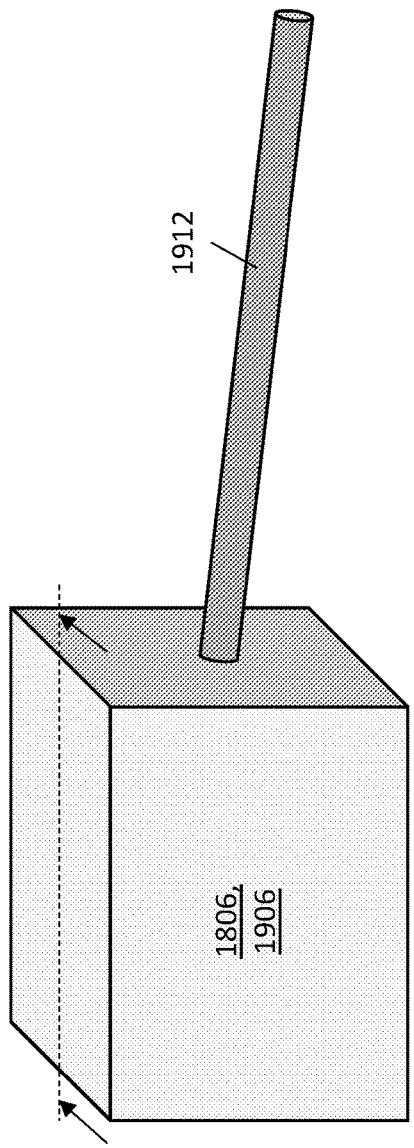
FIG. 22 is a drawing of an operating element used in the sixth and seventh embodiments.
Figure 24:
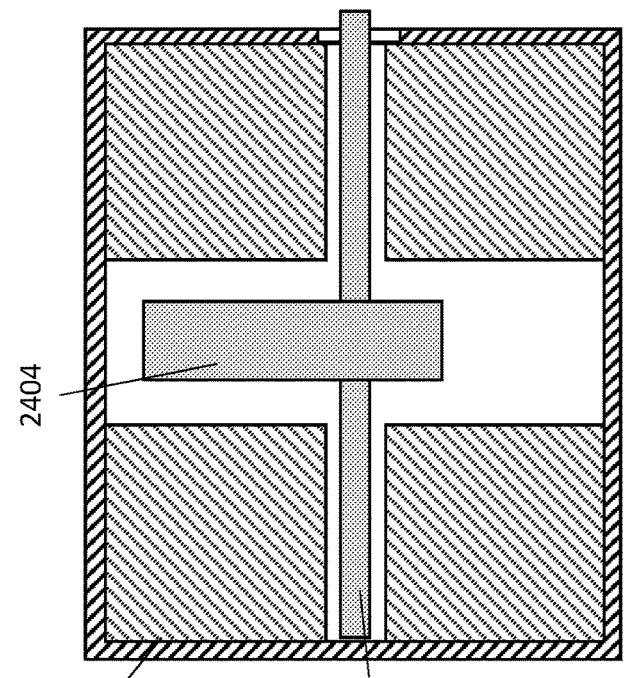
FIGS. 23 and 24 are cross-sectional diagrams of the operating element of FIG. 22, taken along the dotted line and looking in the direction of the arrows.
Figure 23:
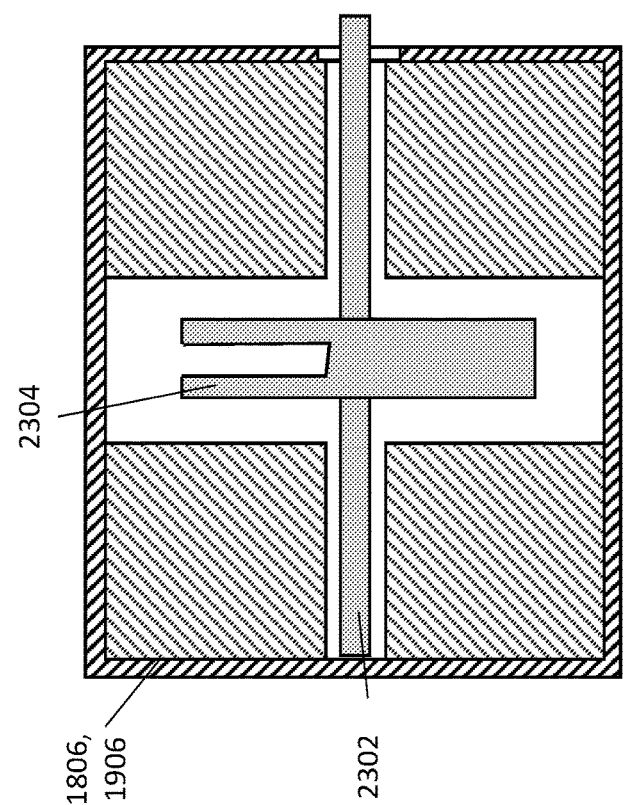

FIGS. 22 to 24 show the front end vibrator box 1806, 1906 in more detail. From these figures, it can be seen that the front end vibrator box comprises a box within which is contained a rotationally mounted weight, the weight distribution of which is eccentric across the weight, as shown in the embodiment in FIG. 23. Here, the eccentric weight distribution is obtained by providing a cut out portion within the weight 2304, which is rotationally mounted on an axle 2302, which is connected to the rotational shaft 1912, or at least the rotational element within the rotational shaft 1912. FIG. 24 illustrates an alternative embodiment, wherein an eccentrically mounted weight 2404 is provided, mounted on a rotational shaft 2402, which is rotationally functionally connected to the rotational element within the flexible drive shaft 1912. In either case, rotation of the flexible drive shaft 1912 causes rotation of the axle 2302, or 2402, rotating the weight 2304, or 2404, and causing the front end vibrator box 1806, 1906 to vibrate.

Figure 26:
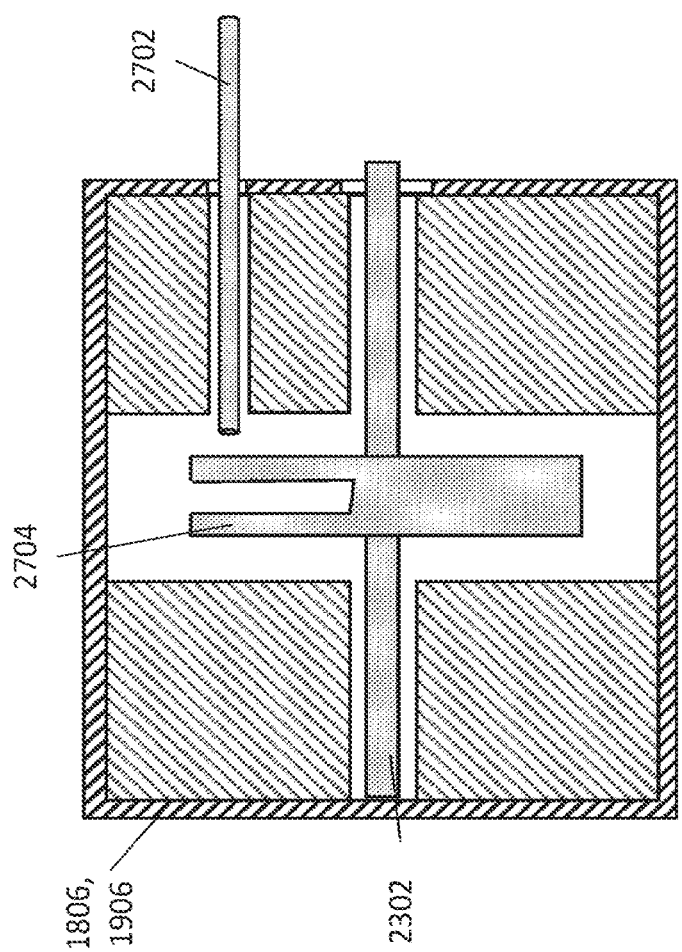
FIG. 26 is a cross-sectional diagram of the operating element of FIG. 22, taken along the dotted line and looking in the direction of the arrows in an embodiment of the invention.
Figure 25:
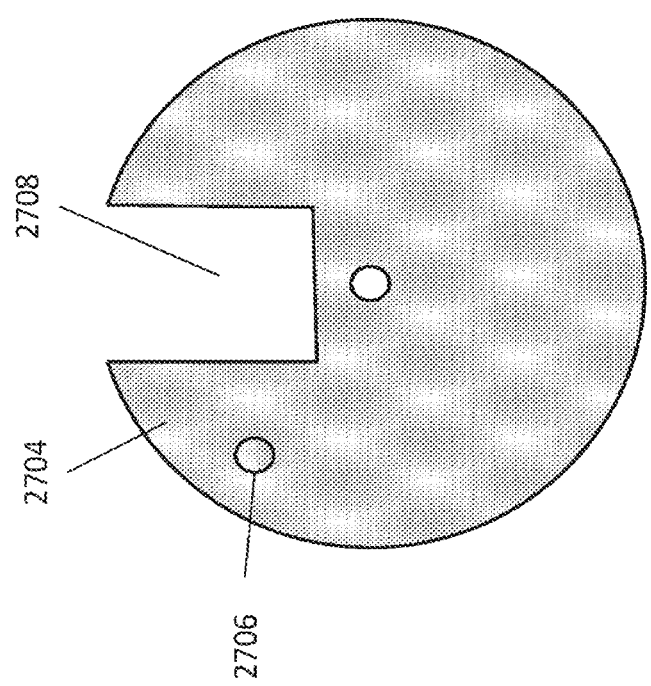
FIG. 25 is a drawing of a rotating weight used in some embodiments of the invention.

FIGS. 25 and 26 show a further embodiment wherein in this case a rotationally mounted weight 2704, having a cut out portion 2708 to give an eccentric weight distribution across its surface, is provided with a reflective portion 2706 on the outer surface thereof. The weight 2704 is rotationally mounted on an axle 2302 within the confines of the vibrator box 1806, 1906, and is driven to rotate by the flexible rotational shaft 1912, as described. However, in this case, an optical fiber 2702 is also fed into the front end vibrator box 1806, 1906, through an aperture therein, so as to shine light on the side surface of the weight 2704. The optical fiber 2702 is respectively positioned with respect to the weight 2704 such that the beam of light from the optical fiber is able to be reflected by the reflector portion 2706 on the side surface of the weight 2704 back into the optical fiber when the reflector portion, which may be a dot, square shape, or the like, is directly in front of the optical fiber 2702. A suitable light detector positioned at the opposite end of the optical fiber 2702 may detect when the reflector portion 2706 reflects light back down the optical fiber. The purpose of this arrangement is to allow the rotational position of the weight 2704 to be determined, in that the precise rotational position of the weight 2704 on the rotational axis of axle 2302 is known when the reflective portion 2706 is directly in front of the optical fiber 2702, and reflecting light back therealong. It can in some circumstances be important to know the position of the rotational weight 2704, to allow repeatability between experiments. Effectively, the reflective portion 2706 rotationally encodes the rotational position of the weight 2704 so that the rotational position can be known and set, which in turn allows the phase of vibrations to be maintained and matched between uses. This is important so that different studies and experiments can be compared with each other.

Figure 27:
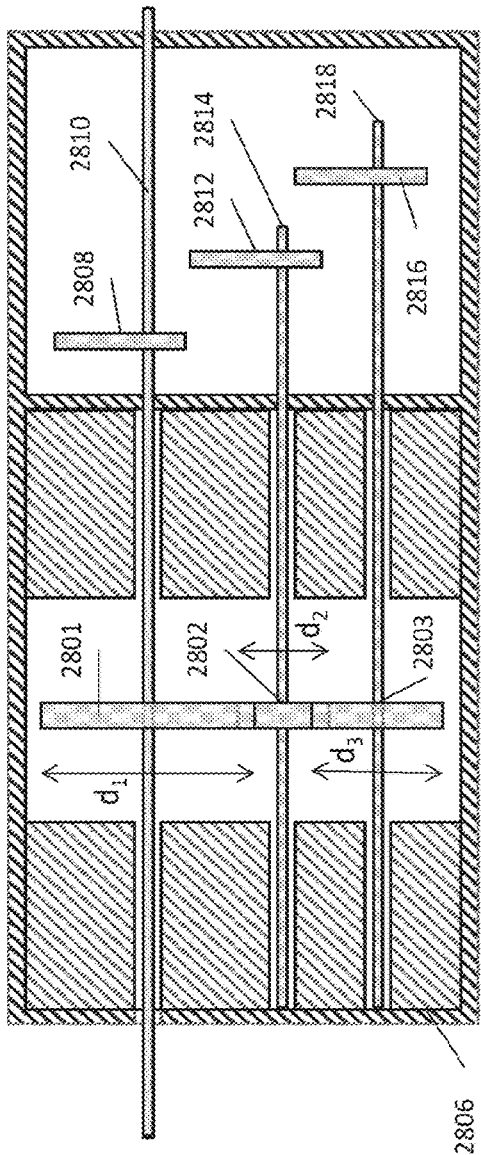
FIG. 27 is a cross-sectional diagram of the operating element of FIG. 22, taken along the dotted line and looking in the direction of the arrows in another embodiment of the invention.
Figure 28:
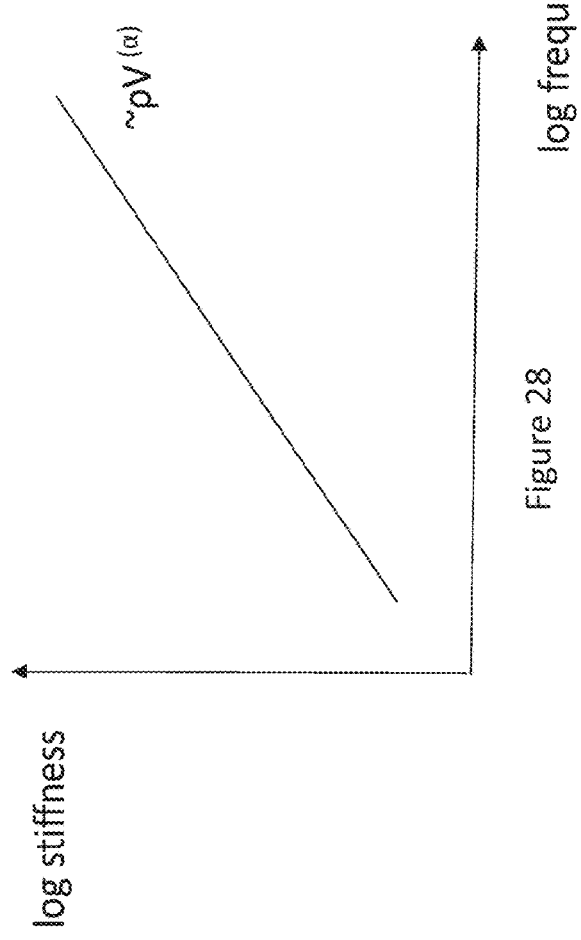
FIG. 28 is a graph showing the relationship between stiffness and vibrational frequency in human tissue.

FIG. 27 illustrates a further embodiment which produces vibrations of more than one frequency, for a given rate of rotation of the rotational flexible drive shaft 1912. Here FIG. 28 illustrates a front end vibrational box 2806, having three rotational axles 2810, 2814, and 2818. The rotational axle 2810, is connected to the flexible rotational shaft 1912, and is driven thereby. Mounted on the axle 2810 is a first gear wheel 2801, having a large diameter D1, for example in the range of 2 cm to 3 cm. The rotational axle 2814 has a second gear wheel 2802, having a small diameter D2, the axle 2814 positioned with respect to the axle 2810 such that the gear wheels 2801 and 2802 mesh. The diameter D2 may be in the range, for example, of 0.75 cm to 1.25 cm. The third rotational axle 2818 is also provided with a gear wheel 2803 mounted thereon, having a diameter D3, which is larger than the diameter D2, but smaller than the diameter D1. For example, D3 may be in the range of 1.25 cm to 2 cm. The rotational axle 2818 is positioned with respect to the rotational axle 2814 such that the respective gear wheels 2802 and 2803 mesh. Respectably mounted on distal ends of the axles 2810, 2814, and 2818 from the gear wheels are eccentrically mounted respective weights 2808, 2812, and 2816. These cause respective vibrational motion when they are rotated on the respective rotational axles 2810, 2814, and 2818.

In use, the rotational axle 2810 is rotated by the flexible rotational shaft 1912, this causing rotation of the eccentrically mounted weight 2808, at a first frequency. The meshing of gear wheels 2801 and 2802 on the respective axles 2810 and 2814 will also cause the rotation of the second rotation axis 2814 at a faster rotational speed than that of the axle 2810. This therefore causes the rotation of eccentrically mounted weight 2812 at the faster rotational speed than that of weight 2808, mounted on the first rotational axis 2810.

Additionally, the meshing of gear wheels 2802 and 2803 between the second and third rotational axles will cause the third rotational axle 2818 to rotate together with the second rotational axle 2814. However, due to the relative diameters of the gear wheels 2802 and 2803, the rotational axle 2818 will rotate at a slower speed than the rotational axle 2814. The eccentrically mounted weight 2816 rotates with the third rotational axle 2818, thus producing vibrations at a third frequency. Taken together, the vibrations produced by the respective rotationally mounted weights 2808, 2812, and 2816 result in vibrations of three different frequencies, which combine to give a complex resultant vibration of the output box as a whole. However, this complex resultant vibration which is transmitted to the object can be detected, and subject to signal processing such as a Fourier transform in the MRI output signal, to resolve the individual vibration frequencies.

The reason why it is important to have multiple frequencies will be apparent from FIG. 28, which shows a graph that maps, on respective log scales, vibrational frequency to stiffness of material, in this case human tissue. From here it can be seen that in tissue the log-log stiffness versus frequency graph is a straight line. Hence, if one can look at different frequencies and determine the stiffness of those different frequencies, then better characterization of the tissue is obtained.

Figure 29:
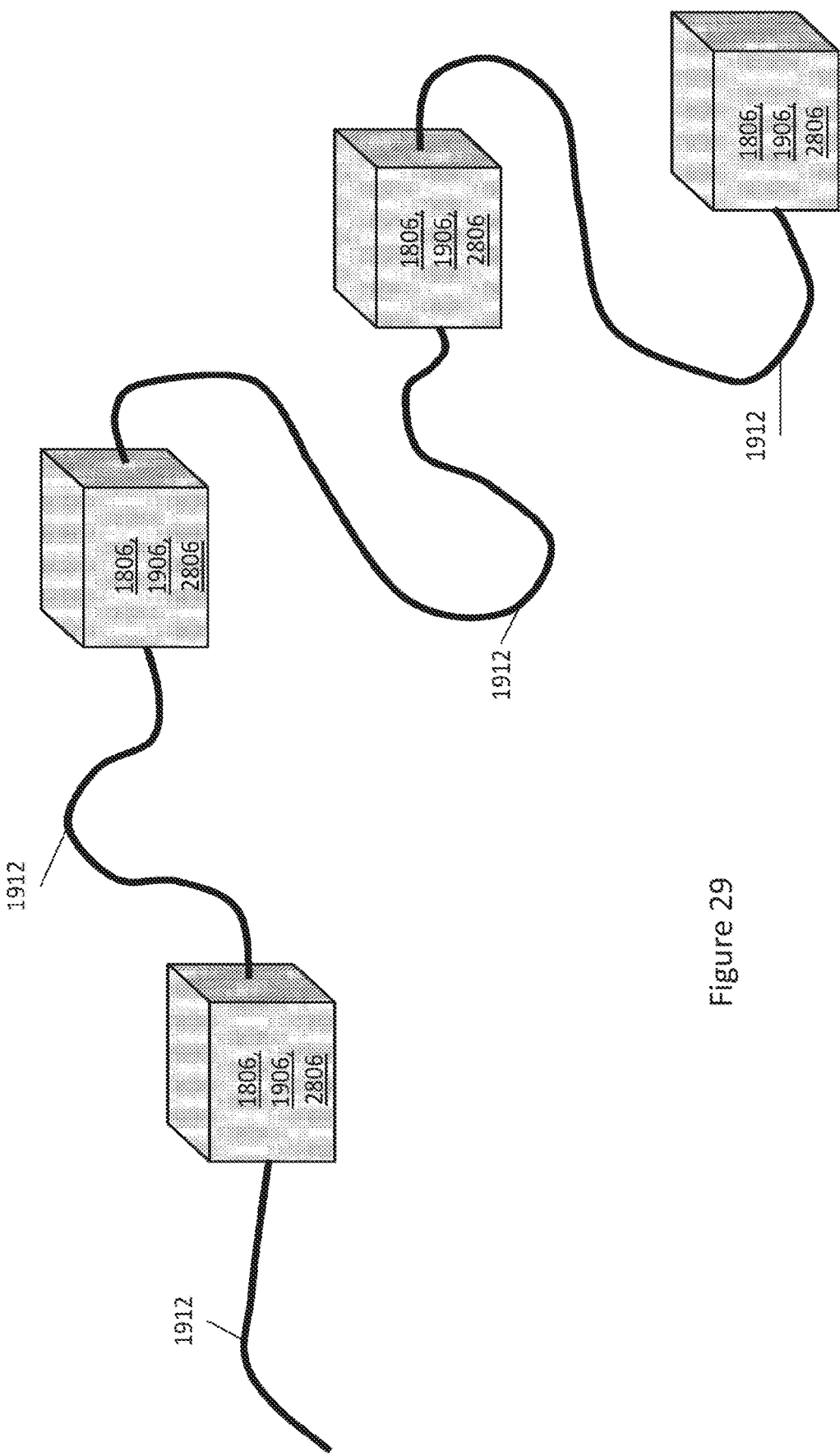
FIGS. 29 to 31 are drawings illustrating various further embodiments of the invention.
Figure 30:
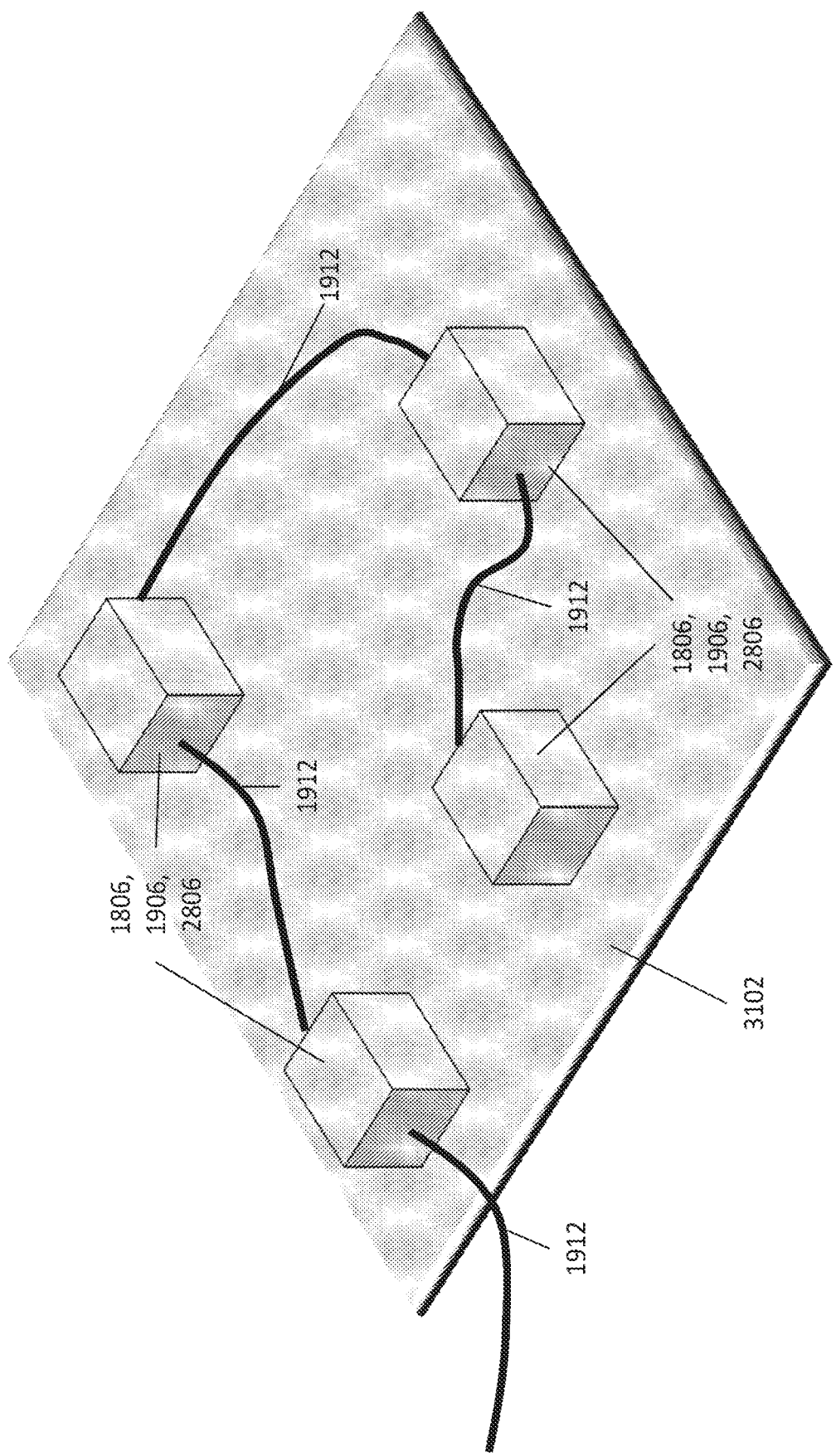
Figure 31:
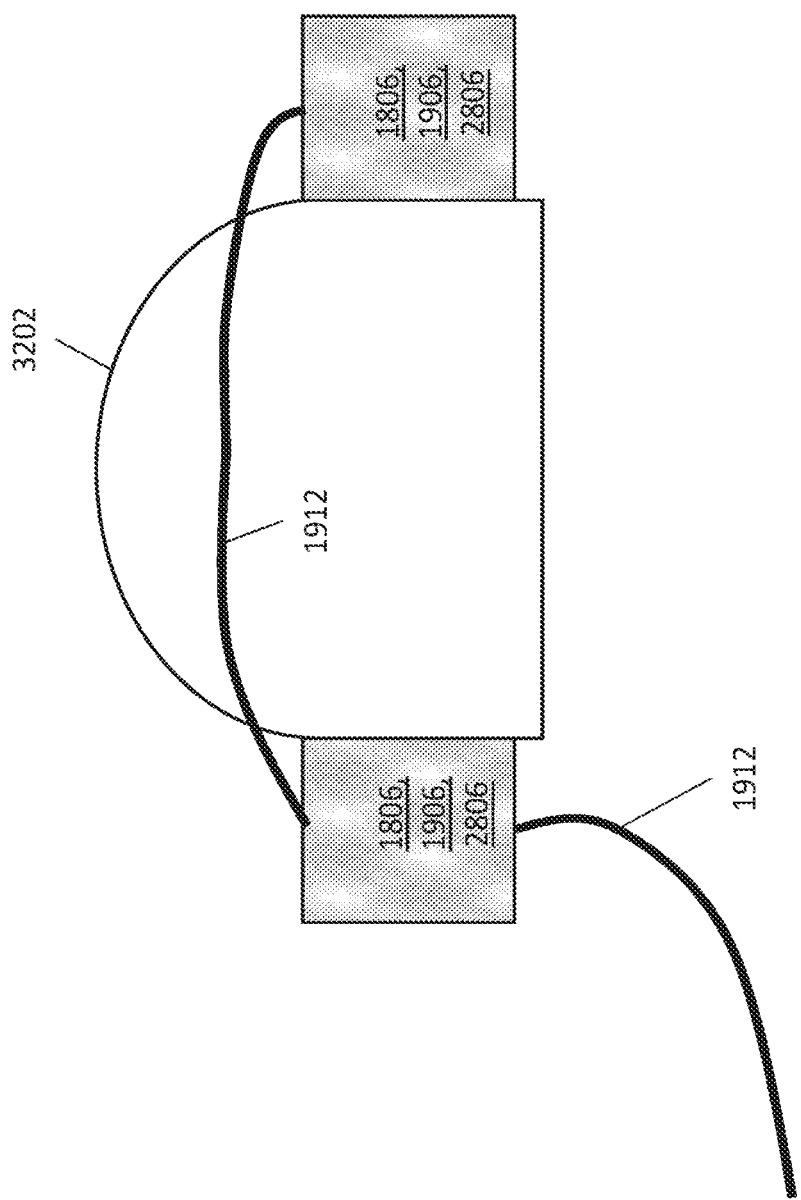

FIGS. 29 to 31 show further embodiments of the invention, provided with multiple vibrator boxes 1806, 1906, or 2806, connected together in series by respective lengths of flexible rotational shafts 1912. The respective lengths of flexible rotational shafts 1912 are connected in series at the respective ends of the drive axles of each vibrator box, so that all of the drive axles and the respective lengths of flexible rotational shaft are driven to rotate simultaneously. That is, a first length of flexible rotational shaft is connected between the drive motor (not shown) and a first one of the vibrator boxes 1806, 1906, 2806 in the series, connecting to a first end of the drive axle of the box. The other end of the drive axle is connected to a second length of flexible rotational shaft, which is in turn connected to a first end of the drive axle of a second vibrator box 1806, 1906, 2806, and so on. In this way a plurality of vibrator boxes may be connected together in series, and driven simultaneously from the same motor.

In addition, the vibrator boxes may be mounted on a substrate, such as a sheet of material, which may be flexible, or a head mount, such as a helmet or flexible cap, as shown in FIGS. 31 and 32 respectively. The advantage of mounting the plural vibrator boxes on a substrate which is then positioned on the subject is that the relative positioning of the boxes with respect to each other can be assured, by their pre-positioning on the substrate. This allows meaningful pre-positions to be set, which are related to anatomically significant points where vibrations should be applied.

Various further modifications, whether by way of addition, deletion, or substitution may be made to above mentioned embodiments to provide further embodiments, any and all of which are intended to be encompassed by the appended claims.

The invention claimed is:

1. A magnetic resonance (MR) compatible transducer system for magnetic resonance elastography, comprising:
 a rotationally mounted eccentric mass arranged to rotate within a container having at least one outer surface that in use transmits vibrations to contacting objects; and
 a flexible drive shaft functionally connected to the rotationally mounted eccentric mass and arranged to impart rotational energy to the rotationally mounted eccentric mass, wherein the rotationally mounted eccentric mass, the container, and the flexible drive shaft are made from MR compatible material, and wherein the flexible drive shaft comprises a flexible rotating core within a flexible non-rotating sheath,
 wherein the MR compatible transducer is configured to determine the rotational position of the rotationally mounted eccentric mass about its rotational axis, whereby a phase of vibrations is maintained and matched between subsequent uses of the MR compatible transducer.

2. The MR compatible transducer according to claim 1, further comprising gears between the flexible drive shaft and the rotationally mounted eccentric mass, such that the rotationally mounted eccentric mass is driven by the flexible drive shaft via the gears.

3. The MR compatible transducer according to claim 1, wherein the flexible rotating core is made from phosphor bronze.

4. The MR compatible transducer according to claim 1, wherein the rotationally mounted eccentric mass comprises a disc-like piece having an unequal mass distribution across its surface.

5. The MR compatible transducer according to claim 1, wherein the rotationally mounted eccentric mass comprises a disc-like piece having one or more portions removed therefrom.

6. The MR compatible transducer according to claim 1, wherein the rotationally mounted eccentric mass comprises a disc-like piece that is rotationally eccentrically mounted such that the rotational axis is not at a center of mass.

7. The MR compatible transducer according to claim 1, further comprising a reflective portion, a light source, and a light collecting arrangement, the reflecting portion positioned on an outer surface of the rotationally mounted eccentric mass and arranged to rotate with the rotationally mounted eccentric mass about its rotation axis, the light source arranged to illuminate the reflective portion, and the light collecting arrangement arranged to collect light from the reflective portion for use in determining the rotational position of the rotationally mounted eccentric mass.

8. The MR compatible transducer according to claim 7, wherein the light source and the light collecting arrangement comprise a common optical waveguide arranged to direct light onto the reflective portion and to collect light reflected therefrom.

9. The MR compatible transducer according to claim 8, wherein the optical waveguide is an optical fiber.

10. The MR compatible transducer according to claim 1, wherein the container has a plurality of rotationally mounted eccentric masses therein, having respective axes so as to permit the plurality of rotationally mounted eccentric masses to rotate at different speeds.

11. The MR compatible transducer according to claim 10, wherein the respective axes have respective gear wheels of different sizes mounted thereon, the arrangement being such that the gear wheels mesh together so as to rotate from a common rotational drive applied to one of the respective axes, to thereby provide the different speeds.

12. The MR compatible transducer according to claim 1, comprising a plurality of containers linked in series by respective lengths of rotational drive shafts such that the containers produce respective vibrational energy from a common rotational drive.

13. The MR compatible transducer according to claim 12, wherein the plurality of containers are mounted in predetermined positions on a substrate whereby to fix the relative positions of the plurality of containers with respect to each other.

14. The MR compatible transducer according to claim 13, wherein the substrate is a sheet of material, preferably of flexible material.

15. The MR compatible transducer according to claim 13, wherein the substrate is a cap-like substrate arranged such that in use it is configured to be worn on a human subject user's head.

16. The MR compatible transducer according to claim 1, further comprising a non-MR compatible motor arranged in use to rotationally drive the flexible drive shaft, the non-MR compatible motor being located outside an MR operating area when the MR compatible transducer is in use.

17. The MR compatible transducer according to claim 1, used to provide controlled and non-distorted oscillating stress to a subject under Magnetic Resonance Elastography (MRE) assessment.

18. The MR compatible transducer according to claim 1, further comprising at least one second rotationally mounted eccentric mass arranged to rotate within the container and being functionally connected to the flexible drive shaft via a first drive arrangement that causes the at least one second rotationally mounted eccentric mass to rotate at a different speed from the first rotationally mounted eccentric mass, whereby to generate simultaneously in use vibrations at at least two different frequencies.

19. The MR compatible transducer of claim 18, further comprising at least one third rotationally mounted eccentric mass arranged to rotate within the container and being functionally connected to the flexible drive shaft via a second drive arrangement that causes the at least one third rotationally mounted eccentric mass to rotate at a different speed from the first rotationally mounted eccentric mass and the second rotationally mounted eccentric mass, whereby to generate simultaneously in use complex resultant vibrations incorporating at least three different fundamental frequencies.

20. A method of providing controlled and non-distorted oscillating stress to a subject under Magnetic Resonance Elastography (MRE) assessment, the method comprising the steps:
attaching a container having a first rotationally mounted eccentric mass arranged to rotate therein to the subject, the container having at least one outer surface that, in use, transmits vibrations to the subject, a flexible drive shaft being functionally connected to the rotationally mounted eccentric mass and arranged to impart rotational energy to the rotationally mounted eccentric mass, wherein the rotationally mounted eccentric mass, the container, and the flexible drive shaft are made from MR compatible material, and wherein the flexible drive shaft comprises a flexible rotating core within a flexible non-rotating sheath;
rotationally driving the flexible drive shaft with a non-MR compatible motor to impart rotational energy to the rotationally mounted eccentric mass and thereby generate non-distorted vibrations that are transmitted by the outer surface of the container to the subject, the non-MR compatible motor being located outside an MR operating area when an MR compatible transducer is in use;
determining the rotational position of the rotationally mounted eccentric mass about its rotational axis; and
maintaining and matching a phase of the vibrations between subsequent uses of the MR compatible transducer.

* * * * *